United States Patent
Badrak et al.

(10) Patent No.: US 10,539,518 B2
(45) Date of Patent: Jan. 21, 2020

(54) X-RAY BASED FATIGUE INSPECTION OF DOWNHOLE COMPONENT

(71) Applicant: Weatherford Technology Holdings, LLC, Houston, TX (US)

(72) Inventors: Robert P. Badrak, Sugar Land, TX (US); Sergey Kolesov, St. Petersburg (RU)

(73) Assignee: Weatherford Technology Holdings, LLC, Houston, TX (US)

( * ) Notice: Subject to any disclaimer, the term of this patent is extended or adjusted under 35 U.S.C. 154(b) by 320 days.

(21) Appl. No.: 15/595,603

(22) Filed: May 15, 2017

(65) Prior Publication Data
US 2018/0328870 A1 Nov. 15, 2018

(51) Int. Cl.
*G01N 23/20* (2018.01)
*G01N 23/207* (2018.01)

(52) U.S. Cl.
CPC ..... *G01N 23/207* (2013.01); *G01N 2223/607* (2013.01); *G01N 2223/6462* (2013.01)

(58) Field of Classification Search
CPC .............. A61B 5/021; A61B 5/02241; G01N 2223/607; G01N 2223/6462; G01N 23/207; G01N 23/20; G01N 23/20025; G01N 21/88; G01N 23/20008; G01N 23/2055; G01N 23/2204; G01N 23/223; G01N 3/32; G01N 23/20016;
(Continued)

(56) References Cited

U.S. PATENT DOCUMENTS

| 5,272,746 A | * | 12/1993 | Isobe | G01N 33/20 |
| | | | | 378/72 |
| 5,625,664 A | * | 4/1997 | Berkley | B23K 31/12 |
| | | | | 378/72 |

(Continued)

FOREIGN PATENT DOCUMENTS

| RU | 152734 U1 | 6/2015 |
| RU | 160151 U1 | 8/2015 |
| SU | 1718068 A1 | 3/1992 |

OTHER PUBLICATIONS

Al-Shorman, M., "Nondestructive residual strain measurement using high energy x-ray diffraction," Graduate Theses and Dissertations, paper 11673, 2008, 287-pgs.

(Continued)

*Primary Examiner* — Irakli Kiknadze
(74) *Attorney, Agent, or Firm* — Blank Rome, LLP

(57) ABSTRACT

Using an X-ray diffractometer, a processing device, and memory, a database models estimates of a number of cycles to failure for each of a plurality of materials. The model estimates are performed on the material at a plurality of applied fatigues up to a failure point and are based on parameters including residual stress, the micro-strain, and the ratio between X-Ray peak intensity and background intensity of the component material. To inspect a component, the material of the component is selected in the database, and measurements are obtained at two or more different depths of at least a portion of the component. Information about current residual stress, micro-strain, and ratio between X-Ray peak intensity and background intensity are determined from the obtained measurements. Then, a fatigue life of the portion of the component is estimated by matching the information to at least one of the modelled estimates of the number of cycles to failure in the database for the selected material.

21 Claims, 13 Drawing Sheets

(58) Field of Classification Search
CPC .... G01N 2203/0075; G01N 2223/053; G01N 2291/0289; G01N 29/043; G01N 29/30; G01N 33/20; G01N 2203/0005; G01N 2203/005; G01N 27/902; G01N 27/9046; G01N 27/72; G01N 27/82; G01N 27/90; G01N 27/904; G01N 17/02; G01N 17/04; G01N 2203/0212; G01N 2223/632; G01N 2291/0231; G01N 2291/0258; G01N 2291/02827; G01L 1/25; G01L 5/0047; G01B 21/30; G01B 7/34; G01B 7/24; G01B 7/16; H01J 2235/081; H01J 2235/086; H01J 35/02; H01J 35/025; H01J 35/08; H01J 35/10; H01J 35/101; H01J 35/16; H01J 35/24; H01J 35/26; G06T 11/206; G06F 17/50

USPC ............. 378/57, 70–85; 250/306; 324/238; 73/602

See application file for complete search history.

(56) References Cited

U.S. PATENT DOCUMENTS

| | | | |
|---|---|---|---|
| 5,793,206 A | 8/1998 | Goldfine et al. | |
| 6,420,867 B1 | 7/2002 | Goldfine et al. | |
| 6,721,393 B1* | 4/2004 | Brauss | G01N 23/20 378/196 |
| 7,159,470 B2* | 1/2007 | Saguto | G01N 3/068 73/779 |
| 7,265,754 B2* | 9/2007 | Brauss | G06T 11/206 345/440 |
| 9,260,200 B1* | 2/2016 | Garratt | G06F 16/26 |
| 2010/0239068 A1* | 9/2010 | Belassel | G01N 3/32 378/72 |
| 2014/0029726 A1* | 1/2014 | Yasukawa | G01L 1/25 378/72 |
| 2015/0146857 A1* | 5/2015 | Fujita | G01N 23/20 378/72 |

OTHER PUBLICATIONS

Monin, V. I. et al., "X-Ray Diffraction Technique Applied to Study of Residual Stresses after Welding of Duplex Stainless Steel Plates," Materials Research, 17(Suppl. 1), dated Jan. 15, 2014, pp. 64-69.

Fisher, J. M., "Cold Work Quality Assessment and Fatigue Characterization Using Conformable MWM(R) Eddy-Current Sensors," 49th Defense Working Group on NDT, Oct. 31-Nov. 2, 2000, 13-pgs.

Jentek Sensors, Inc., "The Leader in Eddy Current Testing Performance," Brochure, copyright 2011.

Goldfine, N. et al., MWM®-Array Electromagnetic Techniques for Crack Sizing, Weld Assessment, Wall Loss / Thickness Measurement, and Mechanical Damage Profilometry, Technical Document, Jentek Sensors, Inc., dated May 2, 2012, 10-pgs.

Kimmel, G. et al., "X-Ray Diffraction (XRD) Characterization of Microstrain in Some Iron and Uranium Alloys," IAEC—Annual Report 1996, pp. 28-56.

Monin, V., "A Portable X-Ray Apparatus for Both Stress Measurement and Phase Analysis Under Field Conditions," JCPDS—International Centre for Diffraction Data 2000,Advances in X-ray Analysis, vol. 43, pp. 66-71.

Prevey, P. S., "Problems With Non-Destructive Surface X-Ray Diffraction Residual Stress Measurement," Lambda Technologies, undated, obtained from www.lambdatechs.com on Apr. 17, 2017, 8-pgs.

Radiatech, LLC, "Non-Destructive X-Ray Crystal Diffraction Analyzer," Brochure, undated, obtained from www.radiatech.ru on Apr. 17, 2017, 2-pgs.

Radiatech, LLC, "X-ray tensometry," webpage, copyright 2016, obtained from www.radiatech.ru on Apr. 17, 2017, 6-pgs.

Radiatech, LLC, "Residual stress in the steel sheet sample produced by Severstal PJSC," paper, undated, obtained from www.radiatech.ru on Apr. 17, 2017, 6-pgs.

Radiatech, LLC, Presentation, undated, obtained from www.radiatech.ru on Apr. 17, 2017, 24-pgs.

Russell, R., et al., "Development of Meandering Winding Magnetometer (MWM®) Eddy Current Sensors for the Health Monitoring} Modeling and Damage Detection of High Temperature Composite Materials," 32nd High Temple Workshop, Feb. 2, 2012, 20-pgs.

Zhao, Y., et al., "Microstrain and grain-size analysis from diffraction peak width and graphical derivation of highpressure thermomechanics," Journal of Applied Crystallography, J. Appl. Cryst. (2008). 41, pp. 1095-1108.

* cited by examiner

X-RAY BASED FATIGUE INSPECTION OF DOWNHOLE COMPONENT

BACKGROUND OF THE DISCLOSURE

Damage from fatigue that can result in product failure if the extent of damage is undetected. Historically, several factors have complicated inspection of fatigue damage in components. For example, physical, traditionally-measurable defects are not formed until well over 50% of the fatigue life is used. At first, the physical defects that do form are very minute. Eventually, the defects grow to an easily-measured size only near the very end of the life cycle when failure becomes eminent. Inspection is also complicated because technicians must first know where to expect fatigue to occur and must then inspect that location or area to look for fatigue damage, such as a growing fatigue crack.

The most prevalent, nondestructive test techniques (NDT) used for surface examination of fatigue include magnetic particle inspection (MPI) and liquid penetrant inspection (LPI). These techniques cannot be used or are not effective in many cases. For instance, a minimum defect size for some components may usually be in the range of about 0.030" or 0.8 microns. The inspection codes for these prevalent test techniques, however, typically consider a minimum size of a relevant defect as being in the range of 0.063" or 1.6 microns. These surface NDT techniques will not reveal indications less than about 0.030" or 0.8 microns. Unfortunately, this means that an actual fatigue crack in a component would only reach the detectable level of these techniques after over 95% of the fatigue life has already passed. As such, these prevalent test techniques would only detect the defect when fatigue failure is close at hand.

In contrast to the prevalent test techniques, eddy current techniques are now available for fatigue inspection. One of the eddy current techniques available is Meandering Winding Magnetometer (MWM) with a multi-frequency scanning eddy current sensor. In proving out of fatigue cracks during the life cycle using this particular eddy current technique on a component, a fatigue crack was observed at the 50% of life range. This observed fatigue crack was not detectable with the MPI and LPI techniques, but was verified via surface examination using a scanning electron microscope (SEM). This same crack was finally detected with the MPI and LPI techniques at a length of about 0.030" at an estimated 95% of the fatigue life used (5% remaining life).

Although these eddy current techniques have some value, they still have some limitations. For example, these eddy current techniques can generally detect fatigue damage at some level in the 30-50% range of the used fatigue life of a component. Yet, wear and mechanical damage of the component tends to introduce more scatter in the results in the eddy current techniques. The introduced scatter of the results interferes with an assessment of the remaining fatigue life of the component. This may be the case where the nondestructive technique works to a large degree, but may prove difficult to actually use in real life applications.

In contrast to the above techniques, it is known that X-ray can be used to measure changes in the strain of a component associated with fatigue damage. The use of strain measured by X-ray to predict fatigue damage level (or status or life) was proposed in 1990, as can be found in the disclosure of SU 1718068. The technology was at least partly defined in this disclosure, but was apparently never put into practice. In fact, even practical aspects of applying X-ray strain measurements to determine fatigue damage level (or life used/remaining) are not disclosed in SU 1718068.

In the X-ray technique of SU 1718068, the life of a component is estimated using micro-strains $\varepsilon$ and their dispersion D. Critical values of the micro-strain $\varepsilon_{cr}$ and the dispersion $D_{cr}$ are determined according to X-ray measurement results. Maximum critical values $\varepsilon^{max}_{cr}$ and $D^{max}_{cr}$ are determined by means of X-ray measurement of a controlled specimen at various surface points. After that, the number of $N_i$ cycles for the specimen's lifetime is determined using a constraint equation. Then, the probability of failure is estimated, and the material lifetime is determined.

The X-ray technique of SU 1718068 has a number of practical disadvantages. First, the technique only uses two parameters (micro-strain and dispersion), which may not give accurate estimates. Second, it is not possible to use the X-ray technique of SU 1718068 without also using an older technique to actually make estimations for real components. For instance, realizing the X-ray technique of SU 1718068 requires using reference samples or requires actually cutting the samples (i.e., destruction of the samples) to achieve measurements. This leads to decreasing accuracy and utility of the technique's estimations. Finally, the X-ray technique of SU 1718068 is not suited for estimating the relative point where the measured component is actually located along a span of fatigue.

The subject matter of the present disclosure is directed to overcoming, or at least reducing the effects of, one or more of the problems set forth above.

SUMMARY OF THE DISCLOSURE

A method according to the present disclosure is implemented using an X-ray diffractometer, at least one processing device, and memory. Each of a plurality of component materials (i.e., samples) are analyzed by obtaining sample measurements of each component material at each of a plurality of applied fatigues up to a failure point of the component material. The sample measurements are obtained using at least two different incident beams of the X-ray diffractometer. As noted below, the at least two different beams are provided at different angles and relate to different penetration depths of the component material. From these sample measurements, the at least one processing device determines sample information about each component material. The sample information includes a sample residual stress at each of the applied fatigues. The sample information also includes sample micro-strains for the component material at each of the applied fatigues and at at least two different depths in the each component material related to the at least two incident beams. (Optionally and as described below, the sample information can include sample X-ray intensities relative to sample background intensities for the component material at each of the applied fatigues.) From the sample information, the at least one processing device then models an estimate of a number of cycles to failure of the component material. The modelled estimates are stored in the memory for each of the component materials for later analysis of a component of interest.

For example, to inspect a component of interest composed of one of the component materials, the modelled estimates are accessed in the memory. One of the component materials is selected in the memory that matches the material for the component to be inspected. Subject measurements of at least a portion of the inspected component are obtained using the at least two different incident beams of the X-ray diffractometer. From the subject measurements, the at least one processing device determines subject information about subject residual stress and subject micro-strain. The at least one processing device estimates fatigue life of at least the portion of the inspected component by matching the subject information to at least one of the modelled estimates of the number of cycles to failure for the selected component material.

From the sample measurements, the at least one processing device can also determine sample information about sample X-Ray peak intensity relative to sample background intensity for use in modelling the estimate of a component material. This sample information about the X-Ray peak intensity relates to the same underlying peak response measured at the two different angles. In this way, the at least one processing device can further determine subject information about subject X-Ray peak intensity relative to subject background intensity for comparison to the modelled estimate from the sample information so the at least one processing device can estimate the fatigue life of a subject component.

In determining the sample information about the sample micro-strains (e.g., the micro-strain values at the two different depths), sample dispersions can also be determined for the sample micro-strains.

In obtaining the sample measurements of the component material using the at least two different incident beams of the X-ray diffractometer, two peak measures can be obtained with the X-ray diffractometer from a same lattice plane simultaneously using a direct beam and an indirect beam for the two different incident beams. The direct beam can include a first incidence angle approximately perpendicular to a surface of the component material, and the indirect beam can include a second incidence angle approximately 50 degrees relative to the first incidence angle. The two different incident beams may respectively correspond to two different depths of penetration beneath a surface of the component material. For example, the two different depths of penetration may respectively correspond to approximately 5-μm and approximately 15-μm.

In this way, the micro-strain determined according to the method can include at least two estimates of micro-strain estimated from the at least two different incident beams corresponding respectively to the at least two different depths of 5-μm and 15-μm; one of these estimates can be used; or an average between the at least two can be used. Likewise, the optional intensity ratio (of the X-ray intensity relative to the background intensity) determined according to the method can include at least two estimates of intensity ratio estimated from the at least two different incident beams corresponding respectively to the at least two different depths of 5-μm and 15-μm; one of these estimates can be used; or an average between the two can be used.

In contrast to estimations of the micro-strains and the intensities at different depths, the residual stress determined according to the method can include one estimate of residual stress estimated from the at least two different incident beams. In particular, the residual stress estimation uses the two peaks from 0° and 50° together by measuring the residual stress value as result of the shifting of the 0° peak in comparison to the 50° peak.

Modelling the estimate can involve constraining the micro-strain according to an equation:

$$\frac{D_{max}^i \cdot \varepsilon_f}{D_f \cdot \varepsilon_{max}^i} = \alpha \cdot \frac{N_i}{N_f} + \beta$$

where: $N_i$—i number of cycles;
$N_f$—number of cycles to failure;
$\varepsilon_f$—micro-strain after failure;
$\varepsilon_{max}^i$—maximal micro-strain at i number of cycles;
$D_f$—dispersion of micro-strain after failure;
$D_{max}^i$—maximal dispersion of micro-strain at i number of cycles; and
$\alpha$ and $\beta$ have values that depend on the specific material type.

In obtaining the sample measurements to model the estimates, the component material can be subject to at least one in-situ condition. Additional information can be collected of the subjected component material under each of the applied fatigues, an effect of the in-situ condition on fatigue failure of the subjected component material can be estimated from the collected information.

For example, the component material can be charged with hydrogen such that collecting and estimating involves collecting additional micro-strains of the charged component material under each of the applied fatigues, and estimating, from the collected micro-strains, hydrogen accumulation effects into grain boundaries and dislocation structure on rapid fatigue failure of the component material. Furthermore, ratios between X-Ray peak intensity and background intensity can be collected of the charged component material under each of the applied fatigues; and hydrogen accumulation effects into single dislocations and point defects on rapid fatigue failure of the component material can be estimated from the collected ratios.

The methods of the present disclosure can be performed by a programmable storage device having program instructions stored thereon for causing a programmable control device to perform the steps of the disclosed method.

A system disclosed herein can be used for inspecting component materials of components. The system includes an X-ray diffractometer, memory, and at least one processing device operatively communicating with the X-ray diffractometer and the memory. The at least one processing device can be configured to perform the disclosed methods.

As a corollary to previous methods, a method of the present disclosure can be implemented using the X-ray diffractometer, the at least one processing device, and the memory. Modelled estimates of a number of cycles to failure for each of a plurality of component materials can be accesses in the memory. One of the component materials can be selected in the memory matching a component for inspection. Subject measurements of at least a portion of the inspected component can be obtaining using the X-ray diffractometer.

From the subject measurements, the at least one processing device can determine subject information about the inspected component. The subject information includes a subject residual stress and includes subject micro-strains (and optionally ratios of X-ray intensities relative to background intensities) and can estimate fatigue life of at least the portion of the inspected component by matching the subject information to at least one of the modelled estimates of the number of cycles to failure for the selected component material.

To obtain the subject measurements of at least the portion of the inspected component, the X-ray diffractometer (or at least elements thereof) can be implemented as an embedded sensor associated with the inspected component or can be implemented as a periodically placed sensor associated with the inspected component. Regardless of whether embedded or placed, the disclosed system can assess a level of fatigue damage of the inspected component.

As an embedded sensor, for example, one or more elements of the X-ray diffractometer can be disposed on, embedded into, incorporated into, installed onto, etc. a portion of the inspected component. Additional elements of the system, such as processing device and memory, can also be similarly "embedded." The form of "embedding" used for the X-ray diffractometer and other elements would thereby depend on the type of component to be inspected, the location of surfaces on the inspected component, what the inspected component is used for, and how the X-ray diffractometer as the embedded sensor would be protected, among a number of other practical considerations. When used as an embedded sensor, the disclosed system can estimate the fatigue life of at least a portion of the inspected component by providing real-time feedback as to accumulating fatigue damage.

The foregoing summary is not intended to summarize each potential embodiment or every aspect of the present disclosure.

DETAILED DESCRIPTION OF THE DISCLOSURE

A. Fatigue Inspection System

Figure 1A:
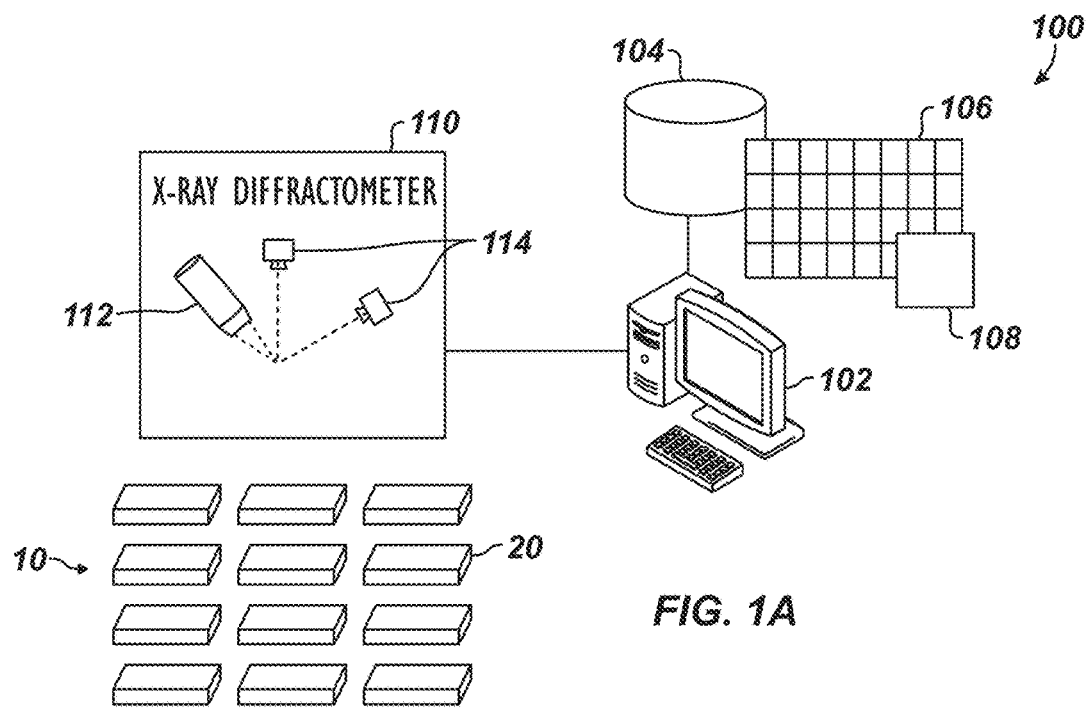
FIGS. 1A-1B schematically illustrate a fatigue inspection system according to the present disclosure in analyzing specimens and inspecting a component of interest.
Figure 1B:
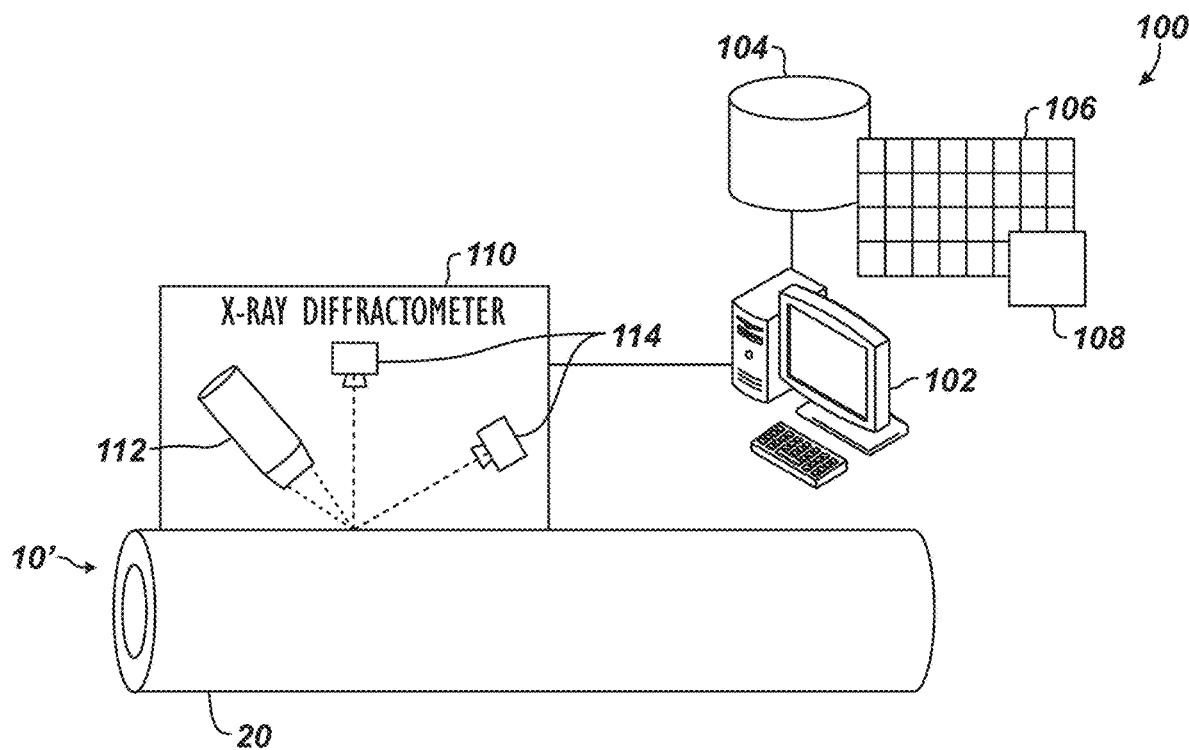

FIGS. 1A-1B schematically illustrate a fatigue inspection system 100 according to the present disclosure. As shown in FIG. 1A, the system 100 is first used for analyzing component materials 20 of various component specimens 10 to develop a database 106 and model 108. Then as shown in FIG. 1B, the system 100 can be used for inspecting fatigue in one of the component materials 20 of a specific component 10' of interest. Any number of specific component 10' can be subject to inspection. In terms of the present disclosure, the component 10' can be a downhole tool, a tool housing, a drillpipe, a drill collar, a component (e.g., housing, rotor, etc.) of a mud motor, a component of a rotary steerable tool, and the like for use in a downhole borehole environment. Such a component 10' can often be reused several times. These types of components 10' can be composed of a metallic component material 20, including, but not limited to, steel, stainless steel, alloy steel, Martensitic steel, Austenitic stainless steel, Inconel®, and the like, which can subject to various levels of fatigue over the life of the component 10' during use. (INCONEL is a trademark of the Special Metals Corporation.)

Accordingly, the subject materials 20 of the specimens 10 can include the same materials of interest found in the components 10' to be inspected. As shown in FIG. 1A, for example, a number of component specimens 10 are composed of the various subject materials 20 of interest to fatigue inspection on downhole components as noted herein. These materials 20 are selected to be a comprehensive representation of the types of metallic materials of components 10' needing fatigue inspection.

The system 100 includes at least one processing device 102, memory 104, and an X-ray diffractometer 110. The processing device 102 can include one or more computers, programmable systems, etc. operably coupled to the memory. As will be appreciated, teachings of the present disclosure can be implemented in digital electronic circuitry, computer hardware, computer firmware, computer software, or any combination thereof. Teachings of the present disclosure can be implemented in a computer program product tangibly embodied in a machine-readable storage device for execution by a programmable processor so that the programmable processor executing program instructions can perform functions of the present disclosure. The teachings of the present disclosure can be implemented advantageously in one or more computer programs that are executable on a programmable system including at least one programmable processor coupled to receive data and instructions from, and to transmit data and instructions to, a data storage system, at least one input device, and at least one output device.

The memory 104 can be any suitable storage device for storing data and can include all forms of volatile and non-volatile memory, including by way of example semiconductor memory devices, such as EPROM, EEPROM, and flash memory devices; magnetic disks such as internal hard disks and removable disks; magneto-optical disks; CD-ROM disks, etc. Any of the foregoing can be supplemented by, or incorporated in, application-specific integrated circuits (ASICs).

As generally depicted, the X-ray diffractometer 110 includes an X-Ray tube 112 appropriate to the material under investigation and includes at least two X-ray sensors 114 of appropriate resolution. In general, the X-ray diffractometer 110 can use known instrumentation to generate, filter, collimate, and direct at least two X-ray beams toward a surface to be investigated. The incident X-ray beams interact with the material, and the sensors 114 of the X-ray diffractometer 110 detect a scattering pattern produced from the at least two X-ray beams interacting with the material 20.

The X-Ray diffractometer 110 is preferably a portable X-Ray diffractometer used to carry out of measurements of required parameters. Being portable, the X-ray diffractometer 110 can be used in the field, on the shop floor, in the laboratory, etc. Teachings related to a portable unit for an X-ray diffractometer are disclosed in Monin, V. et al, "A PORTABLE X-RAY APPARATUS FOR BOTH STRESS MEASUREMENT AND PHASE ANALYSIS UNDER FIELD CONDITIONS," JCPDS-International Centre for Diffraction Data 2000, Advances in X-ray Analysis, Vol. 43, which is incorporated herein by reference in its entirety. The present X-ray diffractometer 110 can use these and additional teachings.

To analyze the laboratory specimens 10 and develop the database 106 and model 108, the system 100 makes measurements of the subject materials 20 of the specimens 10 using the X-ray diffractometer 110 with the specimens 10 subject to controlled levels of fatigue. For example, the specimens 10 can be subject to an increasing number of cycles representative of usage of the specimens 10 that will induce increasing levels of applied fatigue in the subject materials 20 to be measured with the X-ray diffractometer 110.

For its part, the X-Ray diffractometer 110 measures parameters related to residual stress, micro-strain and its dispersion, and optionally a ratio between X-Ray peak intensity and background intensity at each of the different values of applied fatigue up to a point failure on the specimens 10. Preferably, the X-ray diffractometer 110 measures these parameters at least two different depths in the material 20, as detailed later.

In turn, the processing device 102 prepares the database 106 and model 108 for each controlled material 20. The database 106 and model 108 are stored in the memory 104 and describe the evolution of the parameters (related to residual stress, micro-strain and its dispersion, and optionally ratio between X-Ray peak intensity and background intensity) of the subject materials 20 under the different levels of fatigue. The evolution of these parameters then provide estimates of the fatigue life of the subject materials 20 in the model 108.

With the database 106 and model 108 constructed, the disclosed system 100 can inspect a component 10' of interest. As shown in FIG. 1B, for example, at least a portion of the X-ray diffractometer 110 can be implemented as an embedded sensor associated with the inspected component 10' or can be implemented as a periodically placed sensor associated with the inspected component 10'. As a periodically placed sensor, the X-ray diffractometer 110 may be periodically placed on surfaces, locations, and the like of the inspected component 10'. Regardless of whether embedded or placed, the disclosed system 100 can assess a level of fatigue damage of the inspected component 10'.

As an embedded sensor, for example, one or more elements of the X-ray diffractometer 110 can be disposed on, embedded into, incorporated into, installed onto, etc. a portion of the inspected component 10'. Additional elements of the system 100, such as processing device 102 and memory 104, can also be similarly "embedded." The form of "embedding" used for the X-ray diffractometer 110 and other elements would thereby depend on the type of component 10' to be inspected, the location of surfaces on the inspected component 10', what the inspected component 10' is used for, and how the X-ray diffractometer 110 as the embedded sensor would be protected, among a number of other practical considerations. When used as an embedded sensor, the disclosed system 100 can estimate the fatigue life of at least a portion of the inspected component 10' by providing real-time feedback as to accumulating fatigue damage.

As shown in FIG. 1B, for example, the results in the database 106 and the model 108 can be used to inspect the component material 20 of a particular component 10' of interest to estimate the fatigue life of the component 10'. In particular, the measurements of the parameters are carried out on the material 20 of the component 10' using the X-Ray diffractometer 110. Using both a direct (0°) beam and an indirect (50°) beam, the X-Ray diffractometer 110 obtains a residual stress value in one measurement by obtaining two peak measures from the same lattice plane simultaneously. Additionally, the X-Ray diffractometer 110 obtains measurements for the other parameters (i.e., micro-strain and dispersion and optionally intensity ratio) using the direct beam and the indirect beam with different depths of penetration of the X-rays. In a preferred example, the two depths can be about 5-μm and about 15-μm beneath the surface of the component material 20.

The X-Ray diffractometer 110 can obtain measurements of the component 10' in the field or in the laboratory during the course of ordinary inspections. In turn, the processing unit 102 assesses the fatigue life of the component 10' based on the measurements and based on the developed database 106 and model 108. To do this, the system 100 uses techniques disclosed herein to measure fatigue damage of the component 10' and to assess the used/remaining life of the component 10'.

The stress measurements are useful on their own for understanding the mechanism of fatigue. However, in predicting the fatigue state, the present technique use more than just stress measurements. A single strain measurement may predict the fatigue state, but results in scatter that interferes with accurately determining the remaining fatigue life of the component 10'. The combination of both shallow and deeper strain measurements as performed in the present technique accomplishes this task while making the measurements less sensitive to surface damage and surface abnormalities. Furthermore, inclusion of the optional intensity ratios of the X-Ray peak intensity and background intensity at the different depths provides even further detailed information for determining the fatigue damage level.

B. Process of Building Fatigue Inspection Information

With an understanding of the disclosed system 100 and how it is used to first develop information about materials 20 and then is used to inspect components 10' of interest, discussion now turns to the processes involved in the present technique in more detail.

Figure 2:
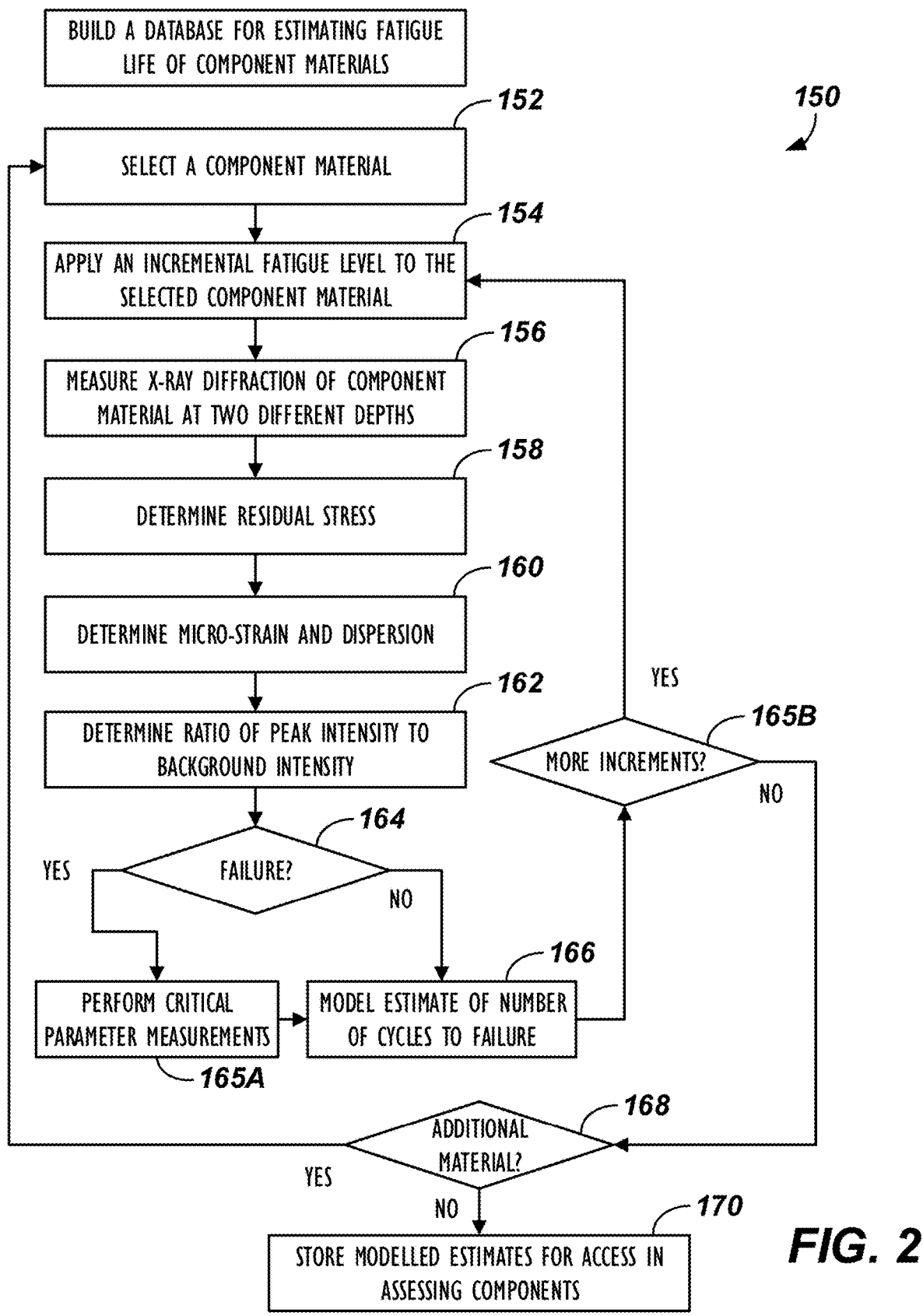
FIG. 2 illustrates a process for building an inspection database and model for component materials of components of interest.

FIG. 2 illustrates a process 150 for building an inspection database 106 of measurements and for building estimation models 108 for the fatigue life of component materials 20 of components 10' of interest. The process 150 uses the X-ray diffractometer 110, the processing device 102, and the memory 104 of the system 100, such as discussed previously.

A sample or specimen 10 is selected from a plurality of component materials 20 of interest for use in analyzing components 10' (Block 152). As noted herein, the various components 10' of interest include tool housings of downhole tools, such as rotary steerable systems; drillpipes; drill collars; etc. The materials 20 can include, but are not limited to, stainless steel, alloy steel, Inconel®, etc. Thus, one of these materials 20 is selected for analysis.

Stress and structure change under levels of fatigue. These are estimated at different structural scale levels based on sample measurements of the specimens 10 by the X-ray technique. The following parameters are used for assessment of the life: (1) a residual stress (or macro level stress) related to the stress condition's evolution in the bulk of the component material 20, (2) micro-strains and their dispersions (or micro level strains) related to the evolution of structure/stress in grain level (grain boundary condition and different dislocations structure), and (3) optionally ratios between X-ray peak intensity and background intensity (or sub-micro level) related to the evolution of the structure/ stress on scale of several atoms (point defects and singe dislocations) of the component material 20.

To model the evolution of these parameters in the material 20, an incremental fatigue level is applied to the selected material 20 (i.e., to the specimen 10 of the material 20) (Block 154). For instance, a first fatigue level of 0% can be used initially. In later stages, fatigue levels can increase by percentage increments up to failure. Overall, the applied fatigue can include a sequence of measurements after application of fatigue to failure, such as 0, 30, 50, 60, 70, 85, and 95% of fatigue to failure. Additional increments of fatigue can be used to refine the sample measurements to failure applied to the specimens 10 of the component material 20. Moreover, more than one specimen 10 of a given material 20 may be analyzed to provide the requisite sample measurements at each increment. Additionally and as noted below, multiple (e.g., three) samples of the material 20 can be cycled to failure so critical parameters can be measured from them. These and other common techniques can be used to refine the sample measurements and results.

In making the sample measurements of the specimen 10, a maximal possible stress value is selected. Fatigue tests are carried out up to the point failure so a number of cycles to failure at a selected load can be estimated for the component material 20 of the specimen 10. Different amounts of fatigue to failure (for example: 0, 30, 50, 70, 80, 90, and 95% cycles to failure) are applied to the specimen 10 of the controlled material 20, and the X-Ray diffractometer 110 measures the selected parameters of interest.

In analyzing the material 20 at the applied fatigue level, sample measurements are obtained at two different depths of the material 20 using the X-ray diffractometer 110 (Block 156). As noted previously, making the sample measurements involves obtaining two peak measures with the X-ray diffractometer 110 from a same lattice plane simultaneously using a direct beam and an indirect beam. The direct beam can have a first incidence angle approximately perpendicular to a surface of the specimen 10, and the indirect beam can have a second incidence angle approximately 50 degrees relative to the surface. Variances in these angles common to the field of measurements in X-ray diffraction can be acceptable to the techniques. In general, the two different depths can be approximately 5-μm and approximately 15-μm beneath a surface of the material 20. Other depths can be used depending on the material 20, and variances in these depths common to the field of measurements in X-ray diffraction and the material of interest can be acceptable to the techniques.

Using the sample measurements at the applied fatigue level, the processing device 102 determines a sample residual stress of the material 20 (Block 158), determines sample micro-strains and dispersions of the material 20 (Block 160), and determines sample ratios between X-Ray peak intensity and background intensity (Block 162).

If the current sample of material 20 is cycled to failure (Yes-Decision 164), then the process 100 performs critical parameter measurements (Block 165A). Either way, the process 100 determines if more increments of applied fatigue need to be analyzed (Decision 165B). In this way, the technique repeats the sample measurements and determination at increased fatigue levels (Block 154) up to the point of failure (YES—Decision 164). At the end of the process 100, the technique has measured a full set of micro-strain evolutions under different fatigue levels for the material 20 in each inspected condition and has measured a full set of intensity ratios evolutions under the different fatigue levels for the material 20 in each inspected condition.

In making the sample measurements, the working surfaces of the specimens 10 are inspected to obtain maximal values of micro-strain and value of residual stress in the same site. Only maximal values of micro-strain may be used for developing the model 108. In particular, a critical micro-strain value ($\varepsilon_{cr}$) is measured on the failure surface of the fatigued specimen 10 of the subject material 20. The measured micro-strain value on the failure surface is a maximum possible value for the sample material 20 in the tested condition. The sample measurements can be carried out on the failure surface that is unprepared when the surface is plain and unraised. Any raised surface may need to be electrically polished before measurements.

As the process 100 in FIG. 2 shows, the destroyed samples cycled to failure (YES—Block 164) have critical values of micro-strain, dispersion, and ratios at two depths measured to give information, such as yield stress for the material, the maximal possible critical values, or the last measurement point in the model (Block 165A). As the process 100 in FIG. 2 also shows, undestroyed samples not cycled to failure (NO—Block 164) are measured to add to the database 106 and the model 108 the values of the parameters at different levels of applied fatigue. Using the set of sample measurements, the evolution of these parameters, and the critical parameter measurements, the processing device 102 models estimates of a number of cycles to failure of the component material 20 relative to measured parameters at the applied fatigue levels (Block 166).

In modelling the estimates (Block 166), the process 100 can analyze the obtained data. If the obtained data is good for a full set of data points including critical values and values at different fatigues, the process 100 proceeds with creating the model 108. Otherwise, the process 100 may need to continue further analysis and obtain additional data for creating the database 106 and the model 108.

As shown in FIG. 2, the entire technique is then performed on specimens 10 of additional component materials 20 in a similar manner (Block 152 to Decision 168) to build the database 106 and estimation models 108, which are stored in the memory 104 (Block 170) for later access in analyzing particular components 10' of interest.

In general, it should be appreciated that multiple samples 10 of the same component material 20 can be analyzed to improve the sample measurements and results. Scatter in sample measurements can lead to additional levels of applied fatigue being used to refine results. It may be desirable to focus particular measurements and analyses in investigating fatigue levels (and associated cycles of life) in which the component material 20 of particular components 10' are expected to operate.

Delving into the details involved in the measurements and determinations of the process 150 of FIG. 2, reference is now made to FIGS. 3A through 7B.

1. Evolution of Fatigue

As noted above, the process 150 for creating the database 106 and the model 108 experimentally assesses the dependences of the parameters including a residual stress measured at different values of applied fatigue, micro-strains (and their dispersions) measured at different values of applied fatigue and at two depths, and optionally intensity ratios measured at different values of applied fatigue and at two depths. The experimentally-assessed dependencies of the parameters at different values of applied fatigue are performed on a number of the subject materials 20 in each condition for getting a comprehensive understanding of how the parameters evolve with fatigue.

Figure 3A:
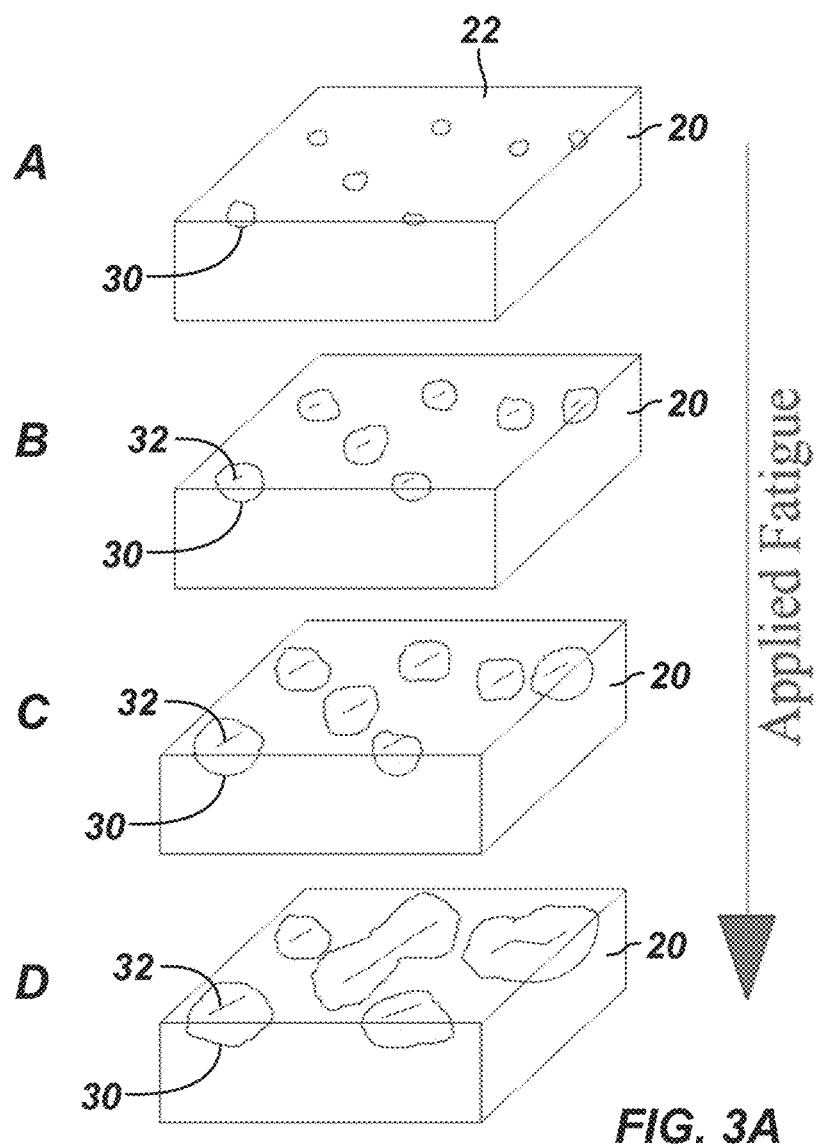
FIG. 3A illustrates evolution of changes to a component material during stages of applied fatigue.

FIG. 3A illustrates evolution of changes to a subject material 20 during stages A-D of applied fatigue. Under less applied fatigue (i.e., stage A), stressed regions 30 may develop at the surface 22 of the material 20 and may not have any significant depth into the material. With more applied fatigue (stages B-C), the stressed regions 30 grow in size and depth in the material 20 and begin to evidence micro-fractures or defects 32. With even more applied fatigue (stage D), the stressed regions 30 combine together. The depth of the regions 30 increase in the material 20, and enlarged micro-fractures or defects 32 are formed.

2. X-Ray Detection of Parameters Related to Fatigue

Figure 3B:
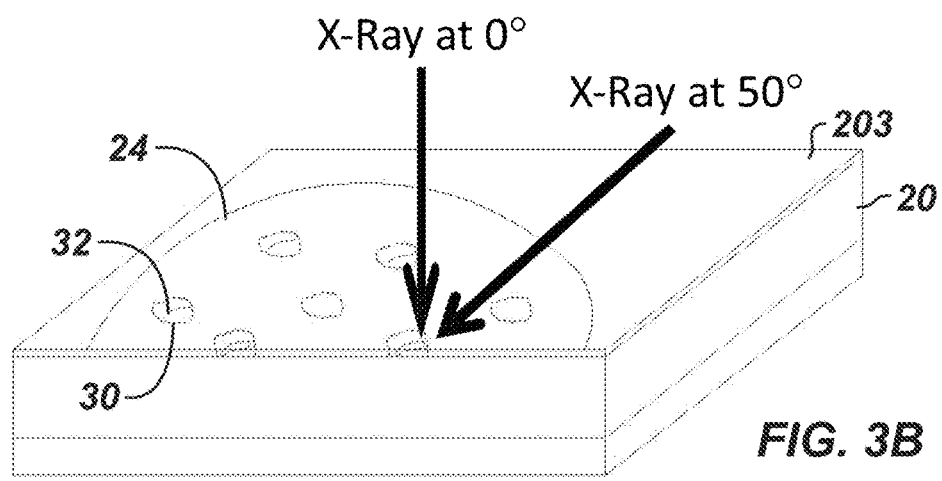
FIG. 3B illustrates the direction of incident X-rays on the surface of the component material in an area under investigation.

FIG. 3B illustrates the direction of incident X-rays on the surface 22 of a subject material 20 in an area 24 under investigation. The surface 22 has stressed regions 30 as shown, which may have defects 32. In the X-ray diffraction, the scattering of the X-rays by the atoms of polycrystalline metallic material of the material produces an interference effect, and the diffraction pattern of that effect gives structural information of the component material 20. Operating as an X-ray tensometer, the present X-ray diffractometer 110 can determine a stress component by measuring the diffraction angles corresponding to reflection from lattice planes with normals characterized by angles ψ1=0-deg. and ψ2=50-deg. Here, "ψ-goniometer" geometry is applied to carry out the stress measurements.

The first incident beam (0-degs.) is orthogonal to the surface 22 and penetrates at a first depth resolution of about 15-μm. The second incident beam (50-degs.) is indirect and penetrates at a second depth resolution of about 5-μm. Using the X-ray diffraction at these different depths can reveal details of the microstructural properties of the subject material 20 used in preparing the database 106 and model 108.

In building the database 106 and model 108, for example, the subject material 20 is subject to physical changes that alter the internal stresses and the microstructural properties of the subject material 20, which can then directly affect the macro-scale properties such as the hardness or strength of the subject material 20. The X-ray beams can measure stress and strain that cause visible changes in the diffraction pattern of the subject material 20. The diffraction pattern consists of peaks from different wavelengths measured at particular diffusional angles relative to the specimen's surface. Changes from stress and strain to the subject material 20 result in differences (asymmetry, broadening, shifting) in the diffraction peak.

Figure 3C:
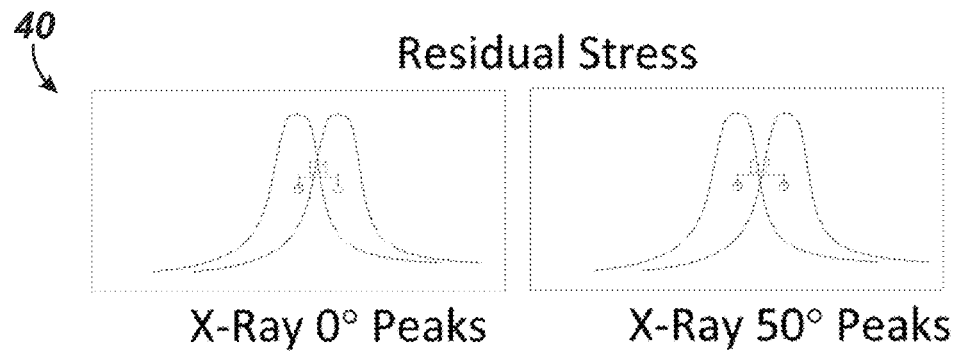
FIG. 3C graphs how residual stress is determined based on the shifting of diffracted peaks of the incident X-ray at the different angles.

For example, FIG. 3C shows graphs 40 depicting how residual stress is determined based on the shifting of diffracted peaks of the incident X-ray at the different angles. In particular, the residual stress estimation uses the two peaks from 0° and 50° together by measuring the residual stress value as result of the shifting of the 0° peak in comparison to the 50° peak.

Figure 3D:
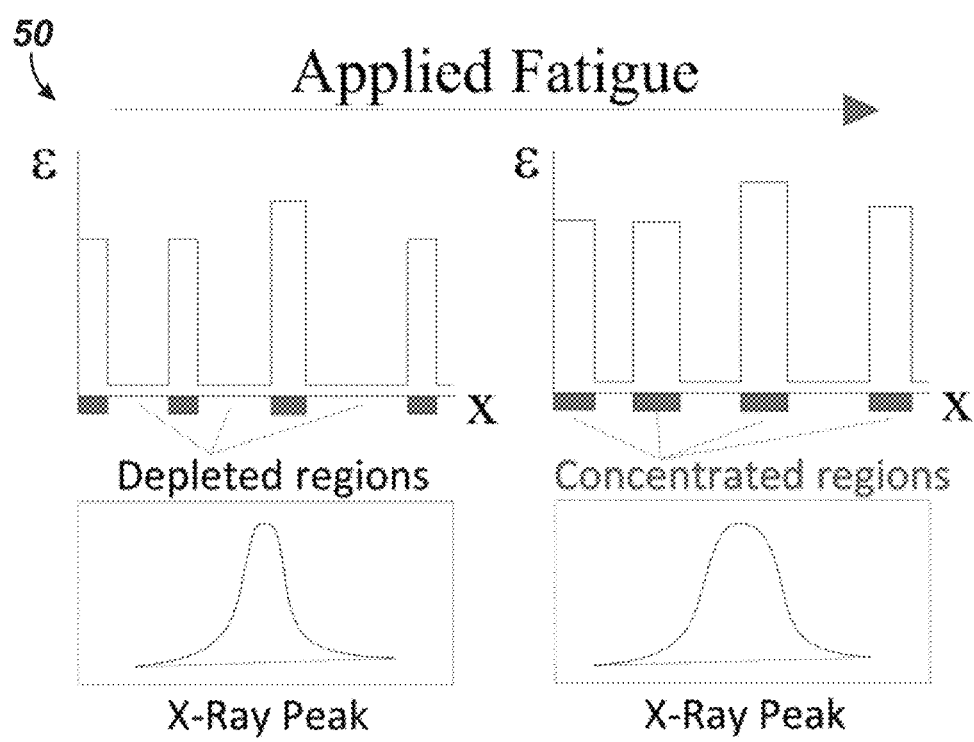
FIG. 3D graphs how strain is determined based on the broadening of the diffracted peaks of the incident X-ray at the different angles.

Additionally, FIG. 3D shows graphs 50 depicting how strain is determined based on the broadening of the diffracted peaks of the incident X-ray at the different angles. The stress-strain surface state changes under fatigue in the metal material 20. The stress is measured by shifting of the X-ray peaks, and the strain is measured by broadening of the X-ray peaks. As shown in FIG. 3C, residual stresses at the different depths are determined by the amount of shifting of the deflected peaks from the respective incident beams. As shown in FIG. 3D, strain is determined by the amount of broadening of the deflected peaks from the respective incident beams, as depleted regions increase to become concentrated regions under applied fatigue.

C. Modelling the Parameters Related to Fatigue

As a result of the measurements, the set of parameters is ready for statistical modelling. According to the present disclosure, there can be three functions (parameters vs number of applied cycles N) that can be obtained from the X-ray measurements for the purposes of modeling estimates of fatigue life for the component materials 20.

First, the residual stress has a particular function (e.g., curve, relationship, etc.) relative to the applied fatigue (e.g., cycles to failure), such that $f_1(N)=f(\text{residual stress})$. One estimate of residual stress can be estimated from the two different incident beams (i.e., 0 and 50-deg. beams). In particular and as noted previously, the residual stress estimation uses the two peaks from 0° and 50° together by measuring the residual stress value as result of the shifting of the 0° peak in comparison to the 50° peak.

Second, the micro-strains have a particular function (e.g., curve, relationship, etc.) relative to the applied fatigue (e.g., cycles to failure) for the at least two depths of investigation, such that $f_2(N)=f(\text{micro-strain})$. Two estimates of the sample micro-strains can be estimated from the two different incident beams (i.e., 0 and 50-deg. beams) corresponding respectively to the two different depths of 5-μm and 15-μm; one of these estimates can be used; or an average between the two can be used.

Third, the intensity ratios have a particular function (e.g., curve, relationship, etc.) relative to the applied fatigues (e.g., cycles to failure) for the at least two depths of investigation, such that $$f_3(N) = f\left(\frac{I_{peak}}{I_{background}}\right).$$

Two estimates of the intensity ratios can be estimated from the two different incident beams (i.e., 0 and 50-deg. beams) corresponding respectively to the two different depths of 5-μm and 15-μm; one of these estimates can be used; or an average between the two can be used.

In the end, the model 108 includes a number of experimental equations that are obtained based on the experimental results. The model 108 includes equations for residual stress evolution and includes equations for micro-strain evolution under fatigue estimated at two depths. Additionally, the model 108 includes equations for evolution of intensity ratios under fatigue estimated at the two depths. The modelled equations are created for each component material 20 in each condition of applied fatigue.

1. Modeling Residual Stress

Figure 4:
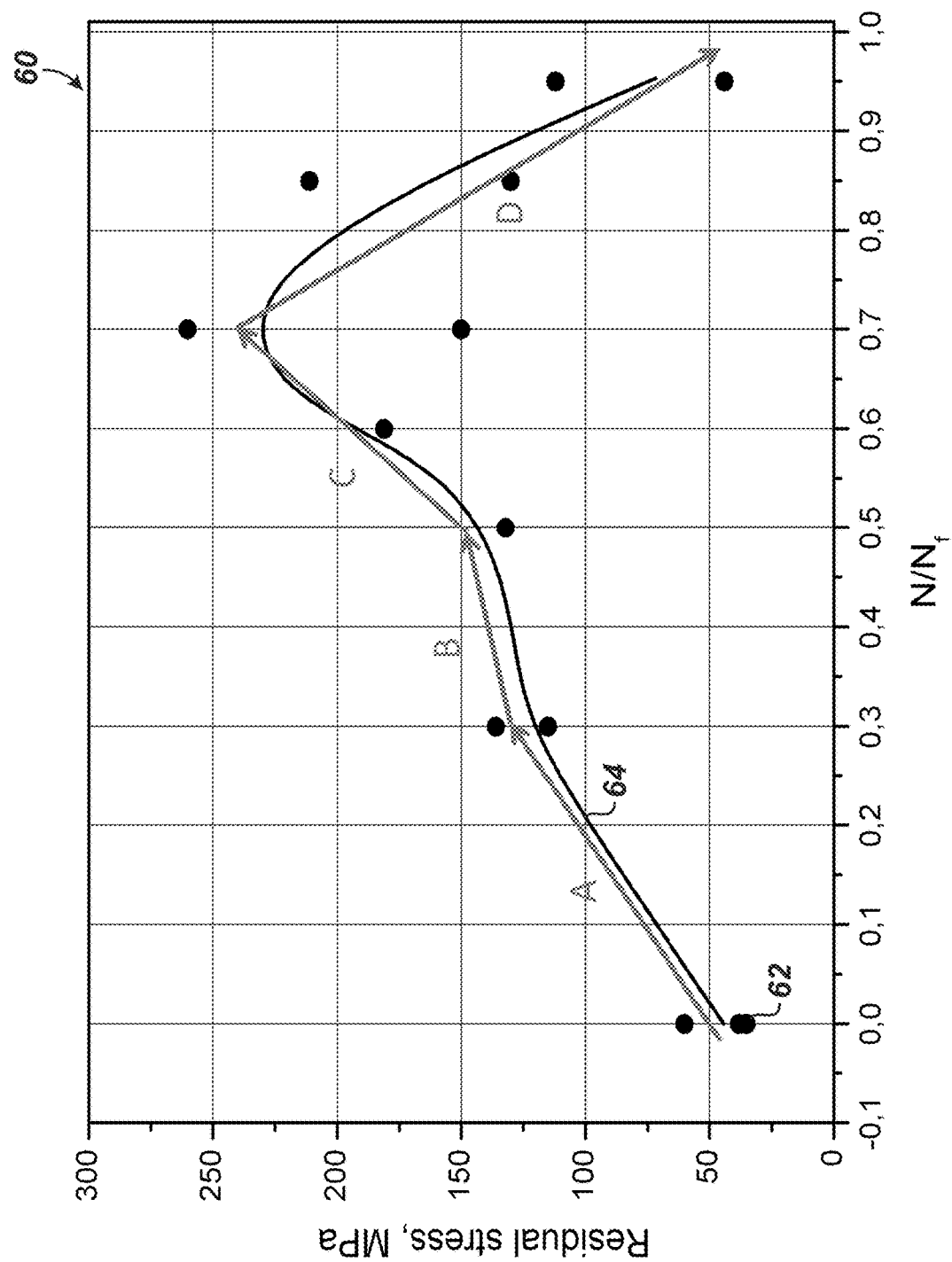
FIG. 4 graphs an example of how residual stress experimentally depends on the number of cycles for a particular component material.

Looking firstly at the residual stress relative to the applied fatigue (e.g., cycles to failure), such that $f_1(N)=f(\text{residual stress})$, FIG. 4 graphs how residual stress experimentally depends on the number of cycles for a particular component material. In this graph, measurements of residual stress 62 are graphed as a function of cycles relative to cycles-to failure $(N/N_f)$. In this example, the component material is INCONEL 718.

Residual stress alters the spacing of the atomic planes in the crystalline material so that a fractional change in the spacing corresponds to the strain. To determine the residual stress values 62 at the applied fatigue level, known X-ray energies are used on the surface of the component material to determine the fractional change in spacing for calculating the residual stress in the component material 20.

In general, residual stress is the compression or tension that remains in the material after the applied force has been removed. The residual stress value increases up to the fatigue crack formation and after that goes down. In the first stage A graphed in FIG. 4, the fatigue forms depleted and concentrated (in form of dislocation loops) dislocation regions. The regions are depicted in stage A of FIG. 3A. In the second stage B graphed in FIG. 4, small defects occur with the dislocation regions as the regions grow under continued fatigue. The regions are depicted in stage B of FIG. 3A.

In the third stage C graphed in FIG. 4, the dislocation regions extend between grains and extend into the material 20 from the surface (increased depth of damage) under continued fatigue. The regions are depicted in stage C of FIG. 3A. Finally, the fourth stage E graphed in FIG. 4, the small defects link up to form cracks under continued fatigue. The regions are depicted in stage E of FIG. 3A.

During the process of testing specimens 10, the residual stress is controlled in the subject material 20 so formation of a fatigue crack can be detected in the specimen 10 when inspected. As shown in FIG. 4, formation of a fatigue crack can be indicated by the sudden dropping in value of the residual stress toward the higher cycles/cycles-to-failure (i.e., region D).

Curve fitting, best-fit analysis, estimation, statistical analysis, matrices, and other numerical methods can be used to express or model the dependence of residual stress on the number of cycles for the particular component material 20. In the graph 60 of FIG. 4, for example, determined values 62 are plotted, and a best-fit curve 64 is fit to the plotted values 62.

2. Modelling Micro-Strain

Figure 5A:
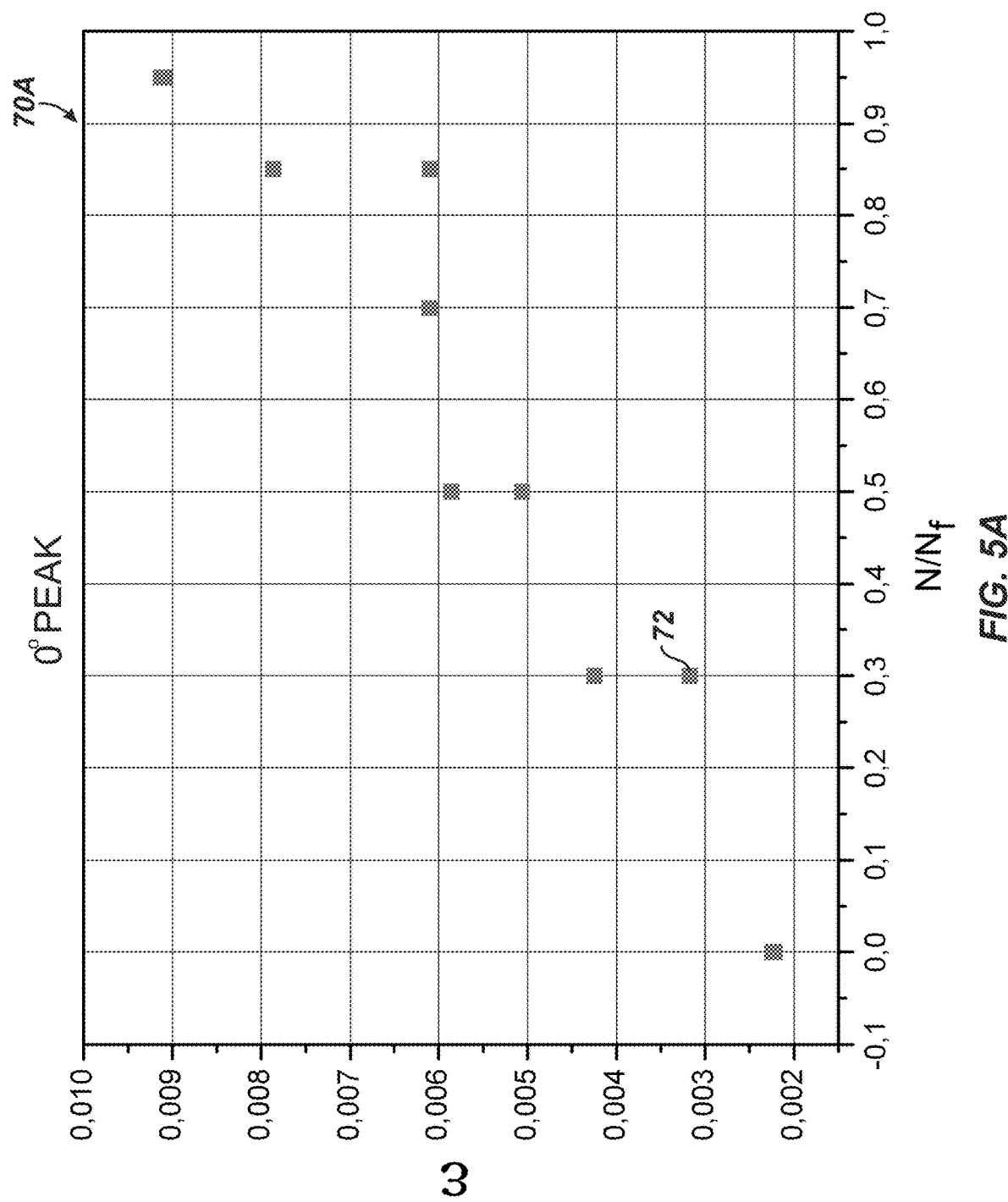
FIGS. 5A-5B and 6A-6B graph examples of how microstrain at two different depths experimentally depends on the number of cycles for the particular component material.
Figure 5B:
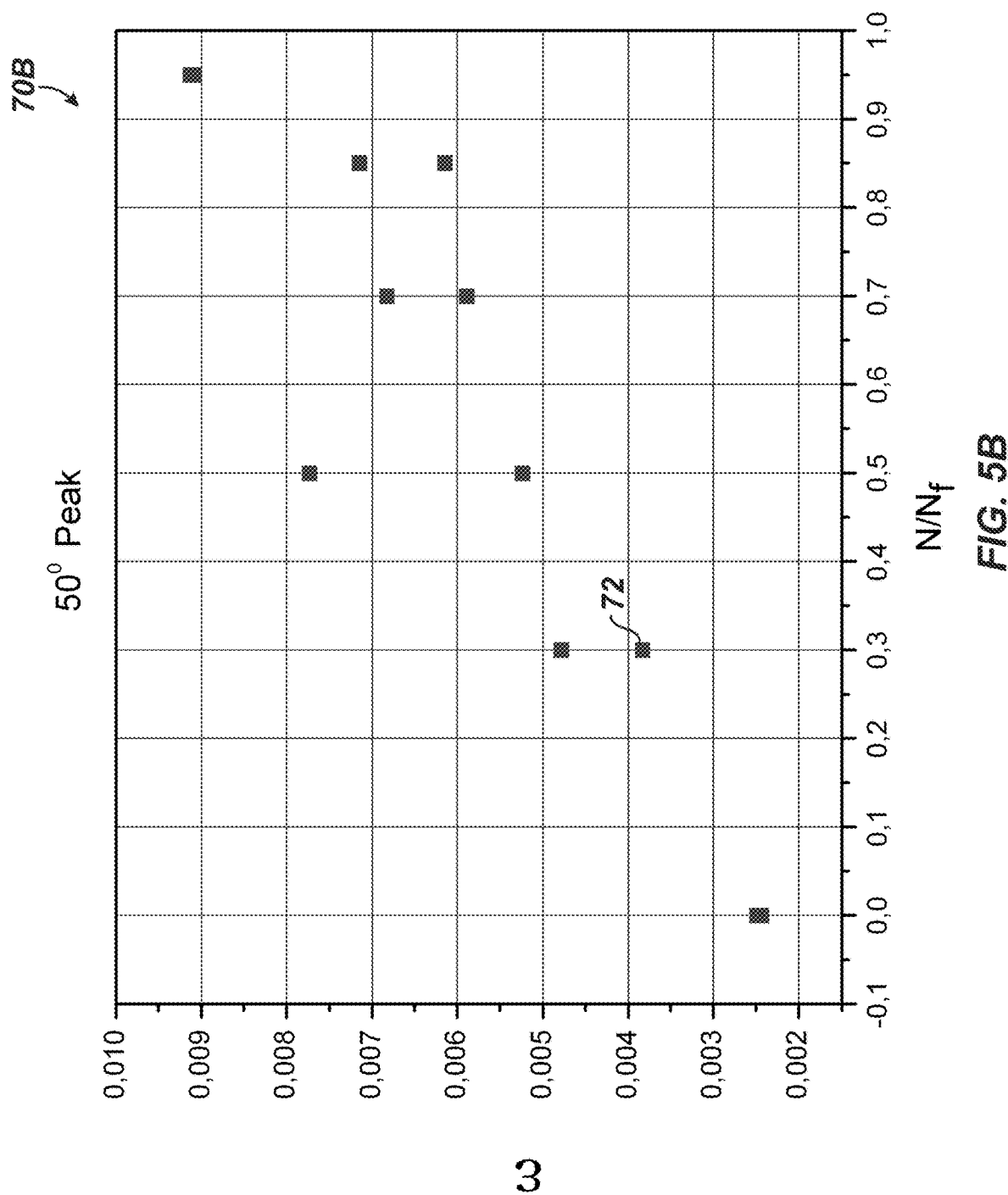

Looking secondly at the relationship of micro-strains relative to the applied fatigue (e.g., cycles to failure) for the depths of investigation, such that $f_2$ (N)=f(micro-strain; estimated on depth 5 and 15 μm), FIGS. 5A and 5B show graphs 70A-B of how micro-strains at two different depths experimentally depends on the number of cycles for the particular component material 20. Again, the component material 20 is Inconel 718 in this example. In FIG. 5A, the penetration depth for direct X-Ray beam is about 15-μm, and the penetration depth for the indirect X-Ray beam is about 5-μm in FIG. 5B.

As noted, the X-ray diffractometer 110 measures parameters related to the strain in the subject material 20. From the measurements, micro-strain values are calculated based on the following equations:

$$\varepsilon = \frac{\beta_i}{4 tg\theta}$$

$$\beta_i = \frac{\int f(x)dx}{f_{max}}$$

where $\beta_i$—integral width of X-Ray peak; θ—Bragg reflection angle.

A full set of micro-strain evolutions under fatigue are measured for each subject material 20 in each inspected condition. Additionally and discussed much later, evolution of micro-strains under fatigue can be collected after hydrogen charging in order to estimate hydrogen accumulation effects into grain boundaries and dislocation structure on rapid fatigue failure of the subject material 20.

Figure 6A:
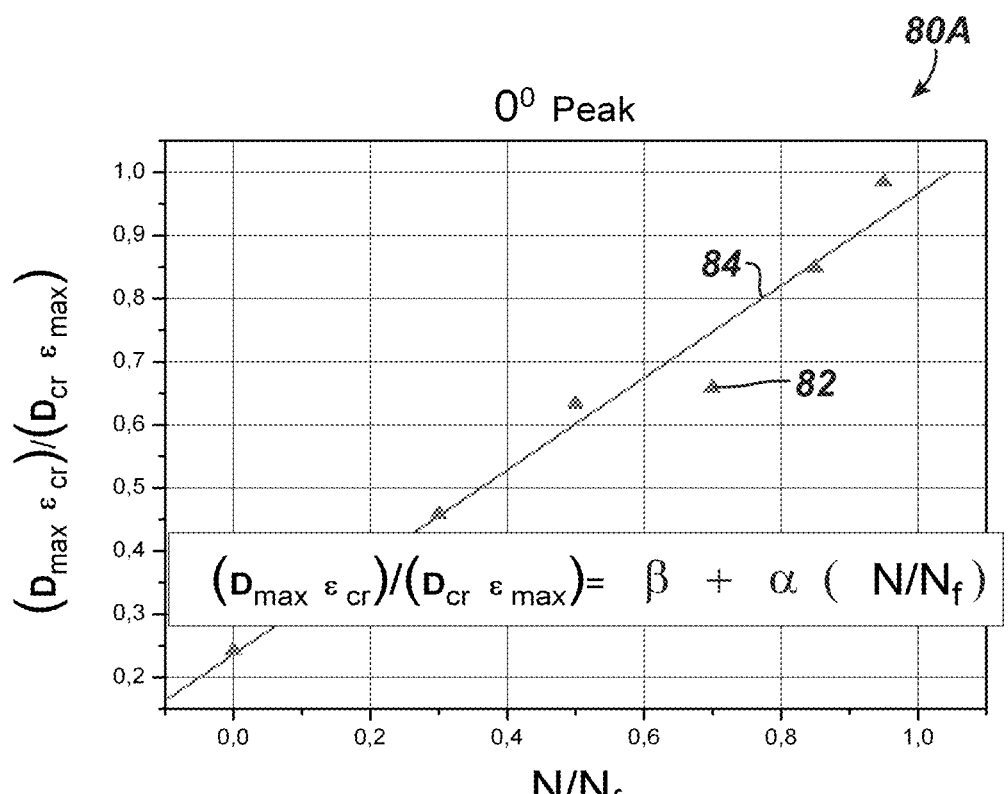
Figure 6B:
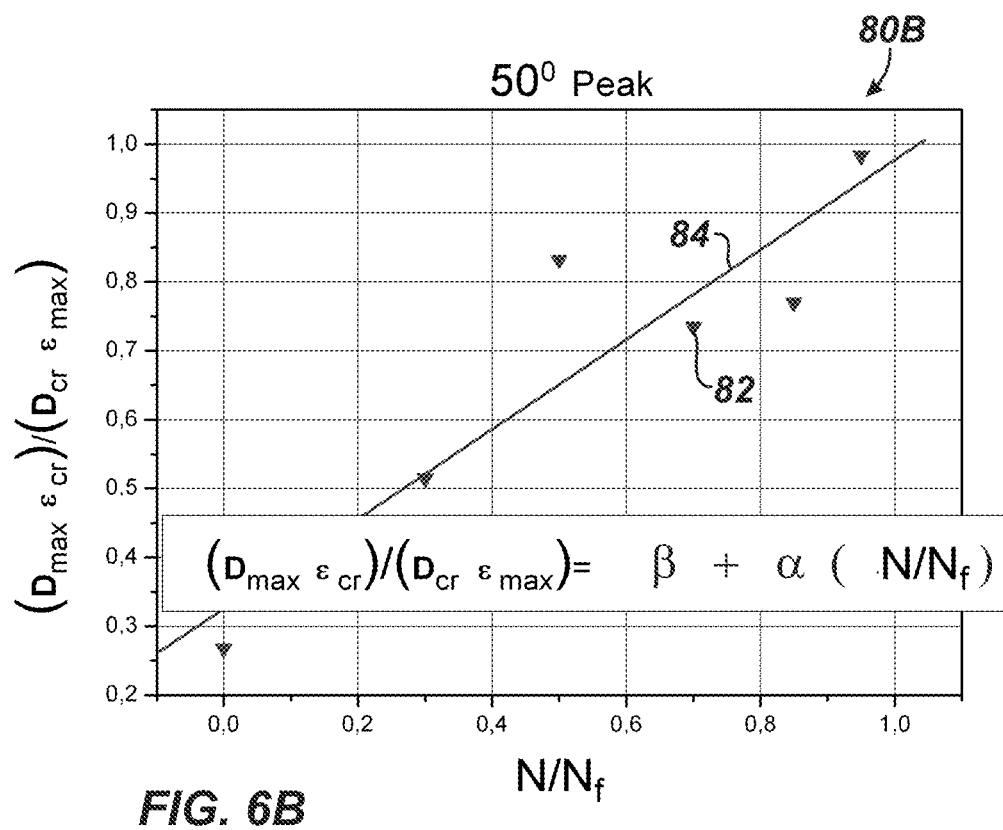

In contrast to the relationship between stress and fatigue as depicted in FIG. 4, the relationship between strain and fatigue damage depicted in FIGS. 5A through 5B can be more linear. As noted, the graph 70A in FIG. 5A shows a first relationship of strain values 72 relative to cycles/cycles-to-failure for the first (0-deg.) incident beam penetrating the surface to a depth of about 15-μm. FIG. 6A shows a modelled line 74 of this first relationship. As noted, the graph 70B in FIG. 5B shows a second relationship of strain values 72 relative to cycles/cycles-to-failure for the second (50-deg.) incident beam penetrating the surface to a depth of about 5-μm. FIG. 6B shows a modelled line 74 of this relationship.

The following equations are used to determine these relationships:

$$\frac{D_{max}^i \cdot \varepsilon_f}{D_f \cdot \varepsilon_{max}^i} = \alpha \cdot \frac{N_i}{N_f} + \beta \quad D = \frac{\beta_i^2}{8tg^2\theta}$$

where: $N_i$—i number of cycles;
$N_f$—number of cycles to failure;
$\varepsilon_f$—micro-strain after failure;
$\varepsilon_{max}^i$—maximal micro-strain at i number of cycles;
$D_f$—dispersion of micro-strain after failure;
$D_{max}^i$—maximal dispersion of micro-strain at i number of cycles; and
α and β have values that depend on the specific material type.

With the experimental results determined as shown in FIGS. 5A-5B, for example, curve fitting, best-fit analysis, estimation, statistical analysis, matrices, and other numerical methods can be used to express or model the dependence of micro-strain on the number of cycles for the particular material. For example, creation of the model involves calibrating the measurements, developing a curve of the experimental results, and reducing the experimental curve to an equation useful in calculating modelled estimates based on input parameters. As shown, the curves or lines 74 in FIGS. 6A-6B are graphed as a function $$\frac{D_{max}^i \cdot \varepsilon_f}{D_f \cdot \varepsilon_{max}^i} \text{ vs } \frac{N_i}{N_f}, \text{ where } \frac{N_i}{N_f}$$

is number of cycles for the material at the two different depths.

3. Modelling Ratio of Intensities

Looking lastly at the optional intensity ratios relative to the applied fatigue (e.g., cycles to failure) for the depths of investigation, such that $$f_3(N) = f\left(\frac{I_{peak}}{I_{background}}; \text{estimated at depth 5 and 15 } \mu m\right),$$

Figure 7A:
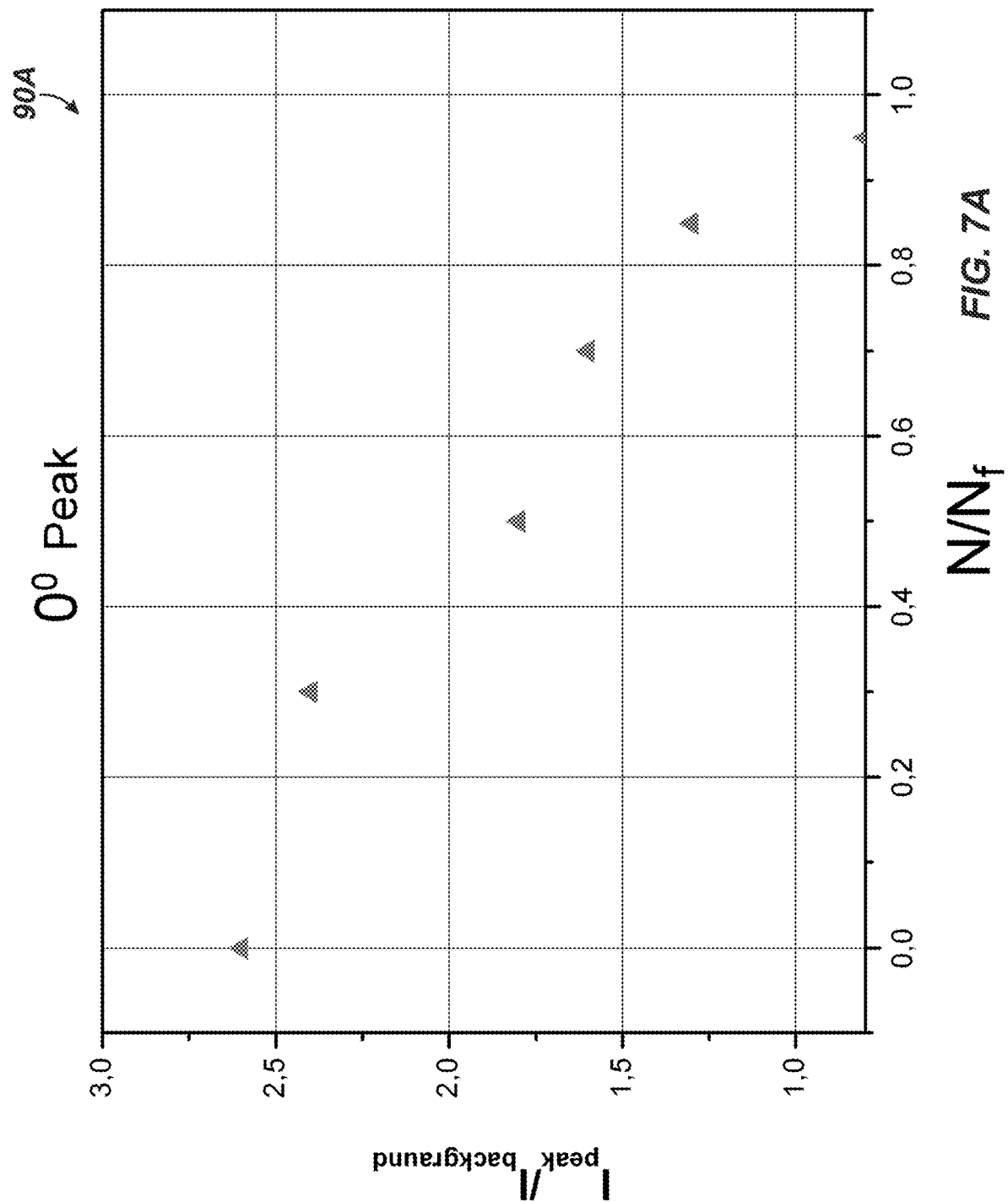
FIGS. 7A and 7B graph an example of how the intensity ratio at two different depths experimentally depends on the number of cycles for the particular component material.
Figure 7B:
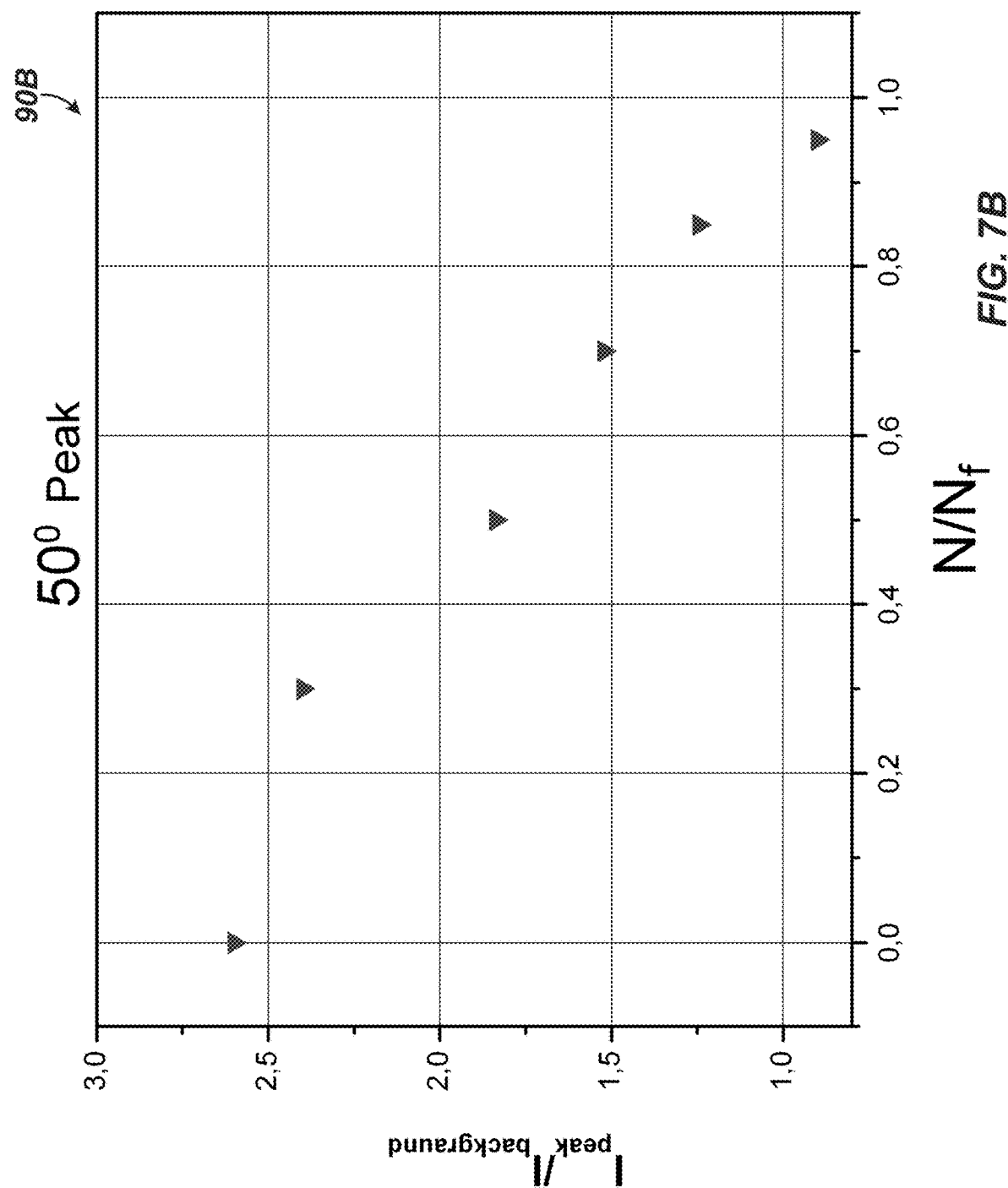

FIGS. 7A and 7B illustrate graphs 90A-B showing how the intensity ratios $I_{peak}/I_{background}$ at two different depths experimentally depends on the number of cycles for the particular component material 20. Again, the component material 20 is INCONEL 718 in this example. In FIG. 7A, the penetration depth for the direct X-Ray beam is about 15-μm, and the penetration depth for the indirect X-Ray beam is about 5-μm in FIG. 7B.

In developing the database 106 and model 108, a full set of $I_{peak}/I_{background}$ evolutions under fatigue are measured for each subject material 20 in each inspected condition. Additionally and as discussed later, evolution of $I_{peak}/I_{background}$ under fatigue be collected after hydrogen charging in order to estimate hydrogen accumulation effects into single dislocations and point defects on rapid fatigue failure of the controlled component material. Again, curve fitting, best-fit analysis, estimation, statistical analysis, matrices, and other numerical methods can be used to express or model the dependence of intensity ratio on the number of cycles for the particular component material.

D. Process of Developing Additional Information of Rapid Fatigue

The above-discussion has described testing specimens 10 of the subject material 20 under fatigue. As will be appreciated, however, a subject material 20 may be subject to rapid forms of fatigue failure due to various environmental factors that can affect the material 20 in situ. Some of these environmental factors can include pressure, temperature, surrounding fluids, etc. Building the database 106 and model 108 can involve subjecting the materials 20 to one or more of these environmental factors to model the fatigue of the subject material 20 under various environmental conditions, such as those encountered downhole in a borehole.

Figure 8:
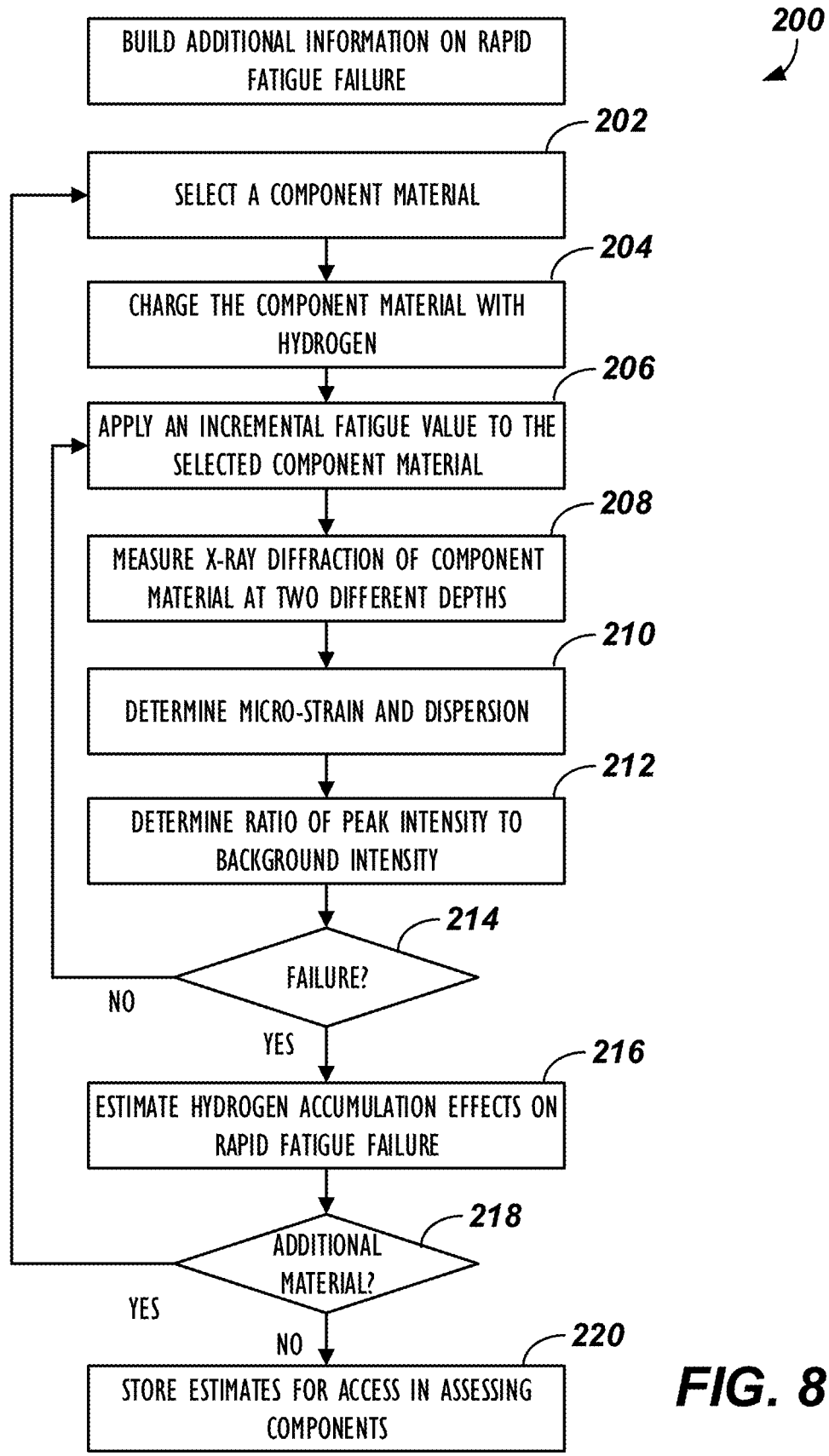
FIG. 8 illustrates an additional process for developing further information for the inspection database and model.

As one example, the effects of hydrogen accumulation on rapid fatigue failure of the subject materials 20 may be of particular interest. To that end, FIG. 8 illustrates an additional process 200 for developing further information of rapid fatigue failure of the component material 20. Following the flow of the previous process 150 of FIG. 2 in which a specimen 10 having a component material 20 is selected, the material 20 in the present process 200 is charged with hydrogen (Block 204). Following comparable steps as before, fatigue levels are applied, and measurements and determinations of micro-strain, its dispersion, and intensity ratio are made up to the point of rapid failure (Block 206 to Decision 214).

From the collected micro-strains of the charged material 20, the processing device 102 can estimate the effects of hydrogen accumulation into grain boundaries and dislocation structure on rapid fatigue failure of the component material 20 (Block 216). From the collected intensity ratios, the processing device 102 can estimate the effects of hydrogen accumulation into single dislocations and point defects on rapid fatigue failure of the component material 20 (Block 216). These estimates are repeated for the various component materials 20 (Block 202 to Decision 218) and are stored in the memory 104 (Block 220) for later access in analyzing a particular component of interest.

E. Process of Inspecting Component

With the database 106 and model 108 of measured and determined parameters of the component materials 20 under fatigue built, the X-ray diffractometer 110, the processing device 102, and the memory 104 can now be used to inspect components 10' of interest for what level of fatigue they may have so the remaining life of the inspected components 10' can be estimated. As noted, inspection of downhole components 10', such as tool housings, drillpipes, drill collars, etc., can help operators know the fatigue life of the component 10' before or after use so the operators can make important decisions on how to use or not use the component 10' in various operations.

The system 100 and techniques of the present disclosure can be used for nondestructive examinations of the component 10' and for determining the material lifetime of the component 10'. The teachings of the present disclosure can improve reliability, can provide measurements on real components 10', and can estimate the life of the component material 20.

Figure 9:
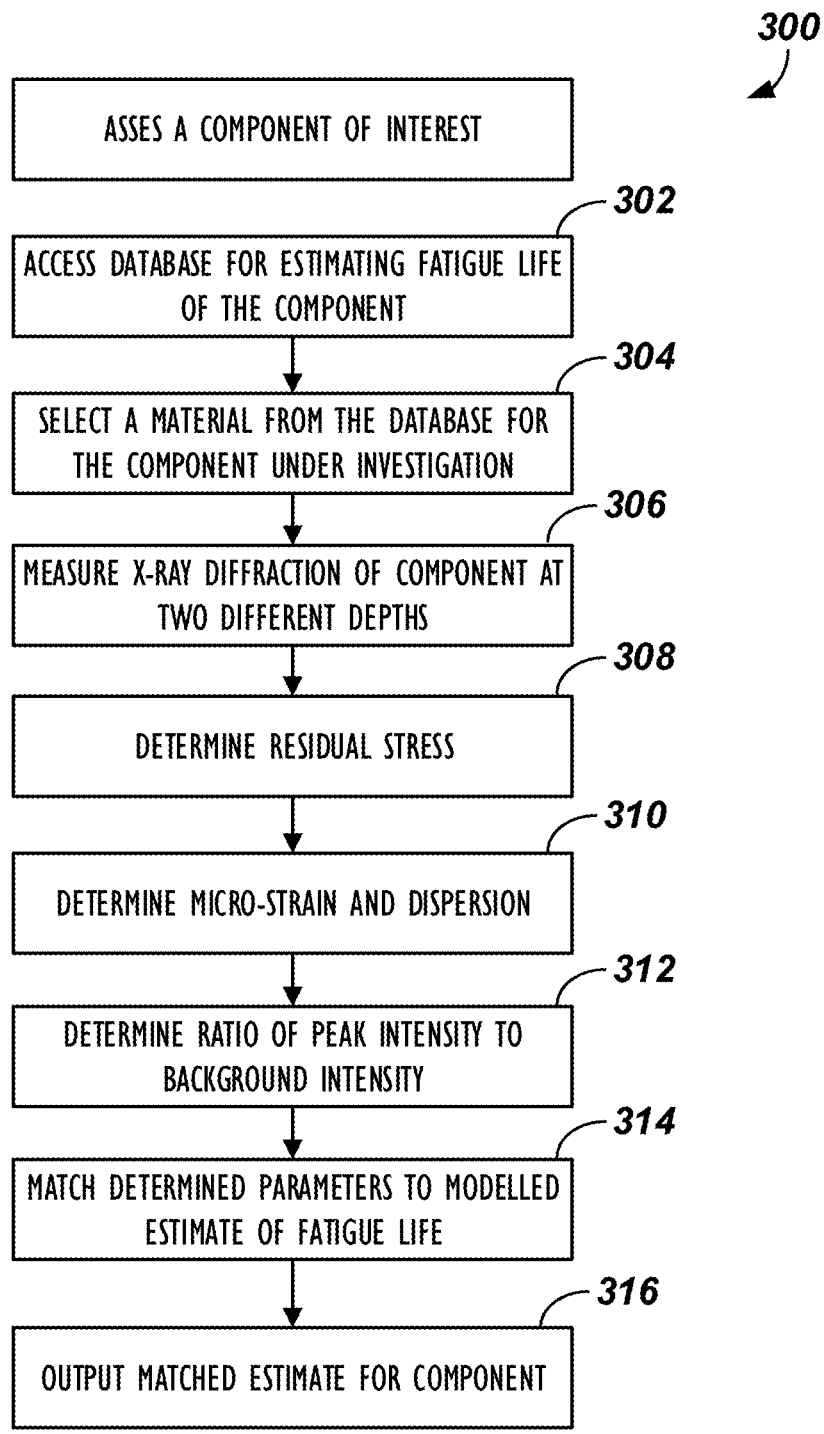
FIG. 9 illustrates a process for inspecting a component of interest using the disclosed system.

FIG. 9 illustrates an inspection process 300 that can be used by operators in the field or in the laboratory to inspect a component 10' of interest using the disclosed system 100. Operators access the database 106 and estimation models 108 (Block 302) and select (or identify) the subject material 20 that matches the component 10' selected for inspection (Block 304). The inspection process 300 now involves subject measurements and determinations of parameters of the identified component material 20 of the inspected component 10' in a comparable manner to those steps used constructing the database and estimation models (Block 306 to Block 3012). However, the component 10' has some unknown level of fatigue, some unknown effect of hydrogen accumulation, and other unknown factors that operators want to assess.

In general, critical sites for fatigue crack formation are preferably inspected on the inspected component 10' to measure a set of the parameters for comparison to the modelled results in the database. Each of the critical sites are inspected by the X-Ray diffractometer 110 preferably without gaps between measurements. The life of the component 10' is assessed based on the statistical model 108 and the results of the measurements.

As noted herein, the measurement and analysis to estimate the life of the inspected component 10' uses at least three parameters, including (1) residual stress, (2) micro-strains and their dispersions estimated at two different depths, and (3) ratios between X-Ray peak intensity and background intensity measured at two different depths. As noted, evolution of these parameters in the component material 20 under fatigue is understood due to the analysis and modeling done on the sample measurements made with the portable X-Ray diffractometer 110 on the specimens 10 of the sample material 20 with different values of applied fatigue (for example: 0, 30, 50, 70, 80, 90, and 95% cycles to failure).

In particular, the inspection process 300 obtains measurements at two different depths of the component material 20 using the X-ray diffractometer 110 (Block 306). From the subject measurements, the processing device 102 determines a subject residual stress, subject micro-strains and their dispersions at two depths, and subject intensity ratios between X-Ray peak intensity and background intensity at two depths (Block 308 to Block 312). These measurement and determinations involve comparable steps outlined previously, as used in obtaining sample measurements and determinations of the samples 10.

Having these determinations, the processing device 102 can now estimate a fatigue life of the inspected component 10' by matching the parameters (the residual stress, the micro-strains and dispersions, and intensity ratios) to the evolution of fatigue in the modelled estimates of the database 106 and model 108 for the selected component material 20 (Block 314). Ultimately, the matched estimate can be output to the operator (Block 316) for the operator to then make a decision on whether to further use the component 10', how to use the component 10', whether to repair or replace the component 10', and any number of other decisions.

In the fatigue life assessment, sorted values of the parameters can be used to estimate the residual fatigue life from the created model 108. The residual fatigue life comes from the estimation of residual stress and micro-strain estimation (measured at two depths) through comparison of the measured parameters of the component 10' to the created model 108. The residual fatigue life can further come from the estimation of the intensity ratio (measured at two depths)

through comparison of the measured parameter of the component 10' to the created model 108. The parameters may further include the further information related to in-situ condition(s), such as hydrogen accumulation.

Figure 10:
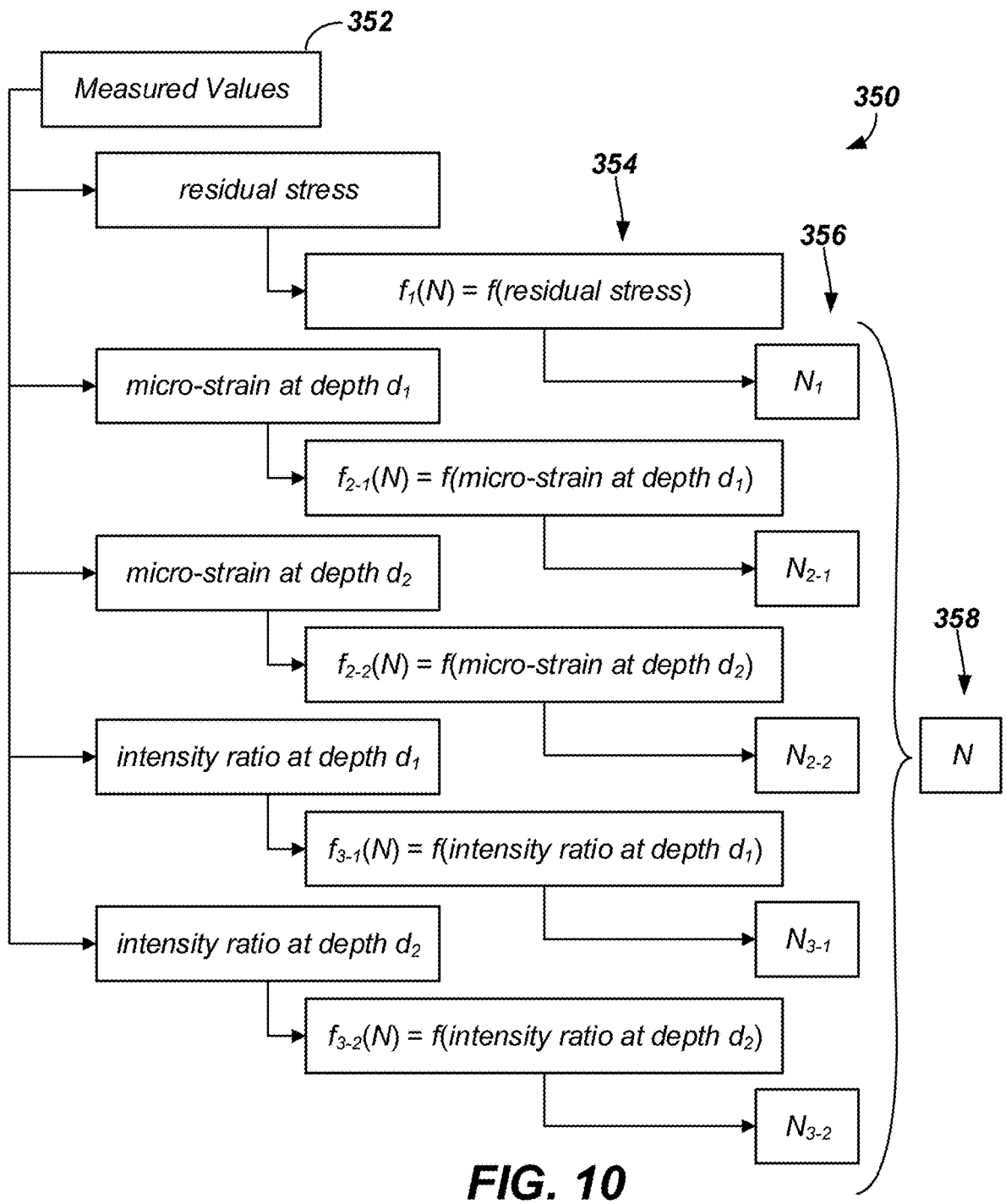
FIG. 10 diagrams how the measured values of a component are compared to the relationships of the parameters to the number of cycles to determine a fatigue life of the component.

FIG. 10 diagrams fatigue life assessment 350 showing how the measured values of the sites of the component 10' are compared to the relationships of the parameters to the number of cycles to determine a fatigue life of the component 10'. As noted, the measured values 352 of an inspected component include residual stress, micro-strain at a first depth, micro-strain at a second depth, intensity ratio at a first depth, and intensity ratio at a second depth. For the component material 20, each of this measured values 352 is compared, matched, found, or the like in the corresponding numerical relationship 354 of the number of cycles relative to the observed information of the parameter. Each comparison would tend to produce a given number of cycles (or fatigue life) 356 of the component 10' of the stated component material 20. These given numbers of cycles 356 may or may not be the same and/or close to one another. Averaging, statistical analysis, weighting, etc. could ultimately be used to estimate a final estimate 358 for the number of cycles (or fatigue life) of the component 10'.

As noted previously, the X-ray technique of SU 1718068 estimates the life of a component by measuring micro-strains E and their dispersion D, and by determining their critical values $\varepsilon_{cr}$ and $D_{cr}$ according to the X-ray measurement results. Maximum values $\varepsilon^{max.}{}_{cr}$ and $D^{max.}{}_{cr}$ are determined by means of the X-ray measurement of the controlled specimen at various surface points. After that, the number of $N_i$ cycles for the specimen's lifetime is determined using a constraint equation. Then, the probability of failure is estimated, and the material lifetime is determined.

As noted, the X-ray technique of SU 1718068 uses only two parameters (micro-strain and dispersion). According to the present disclosure, however, the current technique uses residual stress values and (optionally a ratio between X-Ray peak intensity and background intensity) in addition to micro-strain and dispersion. These additional parameters allow for a more precise estimation of the life of a component 10'.

As also noted, the X-ray technique of SU 1718068 is impractical for estimating the life of real components. The techniques of the present disclosure use an X-ray diffractometer and allow measurements to be made on real components without the need to do destructive testing. Finally, in contrast to the X-ray technique of SU 1718068, the current techniques can be used to construct fatigue curves and to estimate where along the fatigue curve the measured component 10' is situated. Using results of the measurements (or parameters' evolutions) from surface is closer to the real structural evolution in sites of possible fatigue crack formation.

The foregoing description of preferred and other embodiments is not intended to limit or restrict the scope or applicability of the inventive concepts conceived of by the Applicants. It will be appreciated with the benefit of the present disclosure that features described above in accordance with any embodiment or aspect of the disclosed subject matter can be utilized, either alone or in combination, with any other described feature, in any other embodiment or aspect of the disclosed subject matter.

In exchange for disclosing the inventive concepts contained herein, the Applicants desire all patent rights afforded by the appended claims. Therefore, it is intended that the appended claims include all modifications and alterations to the full extent that they come within the scope of the following claims or the equivalents thereof.

What is claimed is:

1. A method implemented using an X-ray diffractometer, at least one processing device, and memory, the method comprising:
   analyzing each of a plurality of component materials by:
      obtaining, using at least two different incident beams of the X-ray diffractometer, sample measurements of the each component material at each of a plurality of applied fatigues up to a failure point of the each component material;
      determining, with the at least one processing device from the sample measurements, sample information about the each component material, the sample information including a sample residual stress at each of the applied fatigues and including sample micro-strains at each of the applied fatigues and at at least two different depths in the each component material related to the at least two incident beams; and
      modelling, with the at least one processing device from the sample information, one or more estimates of a number of cycles to failure for the each component material;
   storing, in the memory, the one or more modelled estimates for each of the component materials; and
   estimating, with the at least one processing device, fatigue life with an estimated number of cycles to failure for at least a portion of an inspected component having a subject material by analyzing the inspected component using the at least two different incident beams of the X-ray diffractometer, and matching a subject residual stress and subject micro-strains of the inspected component to at least one of the one or more modelled estimates for the component material matching the subject material.

2. The method of claim 1, wherein estimating by analyzing and matching comprises:
   accessing, in the memory, the modelled estimates;
   selecting, with the at least one processing device, one of the component materials in the memory matching the subject material of the component for inspection;
   obtaining, using the at least two different incident beams of the X-ray diffractometer, subject measurements of at least the portion of the inspected component;
   determining, with the at least one processing device from the subject measurements, subject information including the subject residual stress of the inspected component and including the subject micro-strains of the inspected component at the at least two different depths related to the at least two incident beams; and
   estimating, with the at least one processing device, the fatigue life of at least the portion of the inspected component by matching the subject information to at least one of the one or more modelled estimates of the number of cycles to failure for the selected component material.

3. The method of claim 2, wherein determining the sample information from the sample measurements further comprises determining sample ratios of X-Ray peak intensity relative to background intensity at each of the applied fatigues and at the at least two different depths in the each component material; and wherein determining the subject information from the subject measurements further comprises determining subject ratios of X-Ray peak intensity relative to background intensity for use in estimating the fatigue life.

4. The method of claim 1, wherein determining the sample information about the sample micro-strains further comprises determining sample dispersions for the sample micro-strains.

5. The method of claim 1, wherein obtaining the sample measurements of the each component material using the at least two different incident beams of the X-ray diffractometer comprises obtaining two peak measures with the X-ray diffractometer using a direct beam and an indirect beam for the at least two different incident beams.

6. The method of claim 5, wherein the direct beam comprises a first incidence angle approximately perpendicular to a surface of the each component material, and wherein the indirect beam comprises a second incidence angle approximately 50 degrees relative to the first incidence angle.

7. The method of claim 5, wherein the at least two different incident beams respectively correspond to at least two different depths of penetration beneath a surface of the each component material.

8. The method of claim 7, wherein the direct beam comprises a first incidence angle approximately perpendicular to a surface of the each component material, wherein the indirect beam comprises a second incidence angle approximately 50 degrees relative to the first incidence angle; and wherein the at least two different depths of penetration respectively correspond to approximately 5-µm and approximately 15-µm.

9. The method of claim 1, wherein modelling the one or more estimates comprises constraining each of the sample micro-strains according to an equation:

$$\frac{D_{max}^i \cdot \varepsilon_f}{D_f \cdot \varepsilon_{max}^i} = \alpha \cdot \frac{N_i}{N_f} + \beta$$

where: $N_i$—i number of cycles;
$N_f$—number of cycles to failure;
$\varepsilon_f$—micro-strain after failure;
$\varepsilon_{max}^i$—maximal micro-strain at i number of cycles;
$D_f$—dispersion of micro-strain after failure;
$D_{max}^i$—maximal dispersion of micro-strain at i number of cycles; and
$\alpha$ and $\beta$ have values that depend on the specific material type.

10. The method of claim 1, wherein determining the sample information from the sample measurements further comprises determining sample ratios of X-Ray peak intensity relative to background intensity at each of the applied fatigues and at the at least two different depths in the each component material for use in modelling the one or more estimates.

11. The method of claim 1, wherein obtaining the sample measurements to model the one or more estimates further comprises:
subjecting the each component material to at least one in-situ condition;
collecting additional information of the each subjected component material at each of the applied fatigues; and
estimating, from the collected information, an effect of the in-situ condition on fatigue failure of the each subjected component material.

12. The method of claim 11, wherein subjecting the each component material to the at least one in-situ condition comprises charging the each component material with hydrogen such that collecting and estimating comprises:
collecting additional sample micro-strains of the each charged component material at each of the applied fatigues; and
estimating, from the collected sample micro-strains, hydrogen accumulation effects into grain boundaries and dislocation structure on rapid fatigue failure of the each component material.

13. The method of claim 12, wherein collecting and estimating further comprises:
collecting additional sample ratios between X-Ray peak intensity and background intensity of the each charged component material at each of the applied fatigues; and
estimating, from the collected sample ratios, hydrogen accumulation effects into single dislocations and point defects on rapid fatigue failure of the each component material.

14. A non-transitory programmable storage device having program instructions stored thereon for causing a programmable control device to perform a method according to claim 1.

15. A system for inspecting component materials of components, the system comprising:
an X-ray diffractometer;
memory; and
at least one processing device operatively communicating with the X-ray diffractometer and the memory, the at least one processing device configured to perform a method according to claim 1.

16. A method implemented using an X-ray diffractometer, at least one processing device, and memory, the method comprising:
accessing, in the memory, modelled estimates of a number of cycles to failure for each of a plurality of component materials;
selecting, with the at least one processing device, one of the component materials in the memory matching a subject material of a component for inspection;
obtaining, using at least two different incident beams of the X-ray diffractometer, subject measurements of at least a portion of the inspected component;
determining, with the at least one processing device from the subject measurements, subject information about the inspected component, the subject information including a subject residual stress and including subject micro-strains at at least two different depths in the inspected component related to the at least two incident beams; and
estimating, with the at least one processing device, fatigue life with an estimated number of cycles to failure of at least the portion of the inspected component by matching the determined subject information to at least one of the modelled estimates for the selected component material matching the subject material.

17. The method of claim 16, wherein determining the subject information from the subject measurements further comprises determining subject ratios of X-Ray peak intensity relative to background intensity at the at least two different depths in the inspected component; and wherein estimating the fatigue life comprises using the subject ratios.

18. The method of claim 16, wherein obtaining the subject measurements of at least the portion of the inspected component comprises implementing at least a portion the X-ray diffractometer as an embedded sensor associated with the inspected component.

19. The method of claim 18, wherein estimating the fatigue life of at least the portion of the inspected component comprises providing real-time feedback as to accumulating fatigue damage.

20. The method of claim 16, wherein obtaining the subject measurements of at least the portion of the inspected component comprises implementing at least a portion of the X-ray diffractometer as a periodically placed sensor associated with the inspected component.

21. The method of claim 16, wherein estimating the fatigue life of at least the portion of the inspected component comprises assessing a level of fatigue damage of the inspected component.

* * * * *